United States Patent
Rulkov et al.

(10) Patent No.: US 9,226,669 B1
(45) Date of Patent: *Jan. 5, 2016

(54) OPTICAL SENSOR FOR A MONITORING DEVICE

(75) Inventors: Nikolai Rulkov, San Diego, CA (US); Mark Hunt, San Diego, CA (US); Donald Brady, Las Vegas, NV (US)

(73) Assignee: Impact Sports Technologies, Inc., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/559,683

(22) Filed: Jul. 27, 2012

Related U.S. Application Data

(63) Continuation of application No. 13/253,046, filed on Oct. 4, 2011, now Pat. No. 8,172,761, and a continuation-in-part of application No. 13/191,907, filed on Jul. 27, 2011, now abandoned, application No. 13/253,046, which is a continuation-in-part of application No. 12/561,222, filed on Sep. 16, 2009, now abandoned, and a continuation-in-part of application No. 11/856,056, filed on Sep. 16, 2007, now Pat. No. 7,625,344, which is a continuation of application No. 11/762,078, filed on Jun. 13, 2007, now Pat. No. 7,468,036, which is a continuation-in-part of application No. 11/388,707, filed on Mar. 24, 2006, now abandoned, and a (Continued)

(51) Int. Cl.
*A61B 5/02* (2006.01)
*A61B 5/024* (2006.01)

(52) U.S. Cl.
CPC ......... *A61B 5/02416* (2013.01); *A61B 5/02427* (2013.01)

(58) Field of Classification Search
CPC .................................................. A61B 5/024
USPC ................ 600/300–301, 310, 323, 481, 483, 600/500–504
See application file for complete search history.

(56) References Cited

U.S. PATENT DOCUMENTS

| | | | |
|---|---|---|---|
| 4,700,708 A | 10/1987 | New, Jr. et al. | |
| 5,830,137 A * | 11/1998 | Scharf ........................... | 600/323 |
| 5,853,364 A * | 12/1998 | Baker et al. .................... | 600/300 |
| 5,873,821 A * | 2/1999 | Chance et al. ................. | 600/310 |
| 6,721,584 B2 | 4/2004 | Baker, Jr. et al. | |
| 7,035,796 B1 | 4/2006 | Zhang et al. | |
| 7,261,690 B2 | 8/2007 | Teller et al. | |
| 7,336,983 B2 | 2/2008 | Baker, Jr. et al. | |
| 7,379,002 B1 * | 5/2008 | Zhixu et al. .................... | 341/143 |
| 7,431,696 B1 * | 10/2008 | Brady et al. ................... | 600/300 |
| 7,468,036 B1 * | 12/2008 | Rulkov et al. ................. | 600/485 |
| 7,720,516 B2 | 5/2010 | Chin et al. | |
| 2001/0049471 A1 | 12/2001 | Suzuki et al. | |
| 2004/0158135 A1 * | 8/2004 | Baker et al. .................... | 600/323 |
| 2004/0186387 A1 * | 9/2004 | Kosuda et al. ................. | 600/502 |
| 2008/0208082 A1 * | 8/2008 | Nysaether et al. ............. | 600/595 |
| 2009/0082994 A1 | 3/2009 | Schuler et al. | |
| 2009/0306736 A1 | 12/2009 | Dobak, III | |

(Continued)

*Primary Examiner* — Patricia Mallari
(74) *Attorney, Agent, or Firm* — Clause Eight IPS; Michael Catania

(57) ABSTRACT

An optical sensor for a monitoring device for monitoring the vital signs of a user is disclosed herein. The optical sensor preferably includes a photodetector and a two light emitting diodes ("LEDs") that emit green light. The optical sensor includes a light barrier that includes multiple walls that block any non-reflected light from the LEDs from transmission to the photodetector so that the photodetector only receives light reflected from the artery of the user resulting in a more accurate detection of the heart rate of the user. A sensor signal from the optical sensor is processed with an accelerometer output signal from the accelerometer to generate a real-time vital sign for a user.

1 Claim, 18 Drawing Sheets

Related U.S. Application Data continuation-in-part of application No. 11/085,778, filed on Mar. 21, 2005, now abandoned, said application No. 13/559,683 is a continuation of application No. 13/312,935, filed on Dec. 6, 2011, now abandoned.

(60) Provisional application No. 61/408,656, filed on Nov. 1, 2010, provisional application No. 61/394,744, filed on Oct. 19, 2010, provisional application No. 61/368,262, filed on Jul. 28, 2010, provisional application No. 61/097,844, filed on Sep. 17, 2008, provisional application No. 60/665,116, filed on Mar. 25, 2005, provisional application No. 60/613,785, filed on Sep. 28, 2004.

(56) References Cited

U.S. PATENT DOCUMENTS

| | | |
|---|---|---|
| 2010/0298655 A1 | 11/2010 | McCombie et al. |
| 2011/0081969 A1 | 4/2011 | Ikeda et al. |
| 2011/0098583 A1 | 4/2011 | Pandia et al. |
| 2011/0118800 A1 | 5/2011 | Sullivan |

\* cited by examiner

OPTICAL SENSOR FOR A MONITORING DEVICE

CROSS REFERENCES TO RELATED APPLICATIONS

The present application is a continuation application of U.S. patent application Ser. No. 13/312,935, filed Dec. 6, 2011, which is a continuation of U.S. patent application Ser. No. 13/253,046, filed on Oct. 4, 2011, which claims priority to U.S. Provisional Patent Application No. 61/408,656, filed on Nov. 1, 2010, and U.S. Provisional Patent Application No. 61/394,744, filed on Oct. 19, 2010. The Present Application is also a continuation-in-part application of U.S. patent application Ser. No. 13/191,907, filed on Jul. 27, 2011, which claims priority to U.S. Provisional Patent Application No. 61/368,262, filed Jul. 28, 2010. The present application is also a continuation-in-part application of U.S. patent application Ser. No. 12/561,222, filed on Sep. 16, 2009, which claims priority to U.S. Provisional Patent Application No. 61/097,844, filed on Sep. 17, 2008, and which is a continuation-in-part application of U.S. patent application Ser. No. 11/856,056, filed Sep. 16, 2007, now U.S. Pat. No. 7,625,344, which is a continuation application of U.S. patent application Ser. No. 11/762,078, filed on Jun. 13, 2007, now U.S. Pat. No. 7,468,036, and which is also a continuation-in-part application of U.S. patent application Ser. No. 11/388,707, filed on Mar. 24, 2006, which claims priority to U.S. Provisional Application No. 60/665,116, filed on Mar. 25, 2005, and which is also a continuation-in-part application of U.S. patent application Ser. No. 11/085,778, filed on Mar. 21, 2005, now abandoned, which claims priority to U.S. Provisional Application No. 60/613,785, filed on Sep. 28, 2004. All of the above mentioned applications are hereby incorporated by reference in their entireties.

STATEMENT REGARDING FEDERALLY SPONSORED RESEARCH OR DEVELOPMENT

Not Applicable

BACKGROUND OF THE INVENTION

1. Field of the Invention

The present invention is related to real-time vital sign monitoring devices. More specifically, the present invention relates to a device for monitoring a user's vital signs that is used in conjunction with a Smartphone.

2. Description of the Related Art

There is a need to know how one is doing from a health perspective. In some individuals, there is a daily, even hourly, need to know one's health. The prior art has provided some devices to meet this need.

One such device is a pulse oximetry device. Pulse oximetry is used to determine the oxygen saturation of arterial blood. Pulse oximeter devices typically contain two light emitting diodes: one in the red band of light (660 nanometers) and one in the infrared band of light (940 nanometers). Oxyhemoglobin absorbs infrared light while deoxyhemoglobin absorbs visible red light. Pulse oximeter devices also contain sensors that detect the ratio of red/infrared absorption several hundred times per second. A preferred algorithm for calculating the absorption is derived from the Beer-Lambert Law, which determines the transmitted light from the incident light multiplied by the exponential of the negative of the product of the distance through the medium, the concentration of the solute and the extinction coefficient of the solute.

The major advantages of pulse oximetry devices include the fact that the devices are non-invasive, easy to use, allows for continuous monitoring, permits early detection of desaturation and is relatively inexpensive. The disadvantages of pulse oximetry devices are that it is prone to artifact, it is inaccurate at saturation levels below 70%, and there is a minimal risk of burns in poor perfusion states. Several factors can cause inaccurate readings using pulse oximetry including ambient light, deep skin pigment, excessive motion, fingernail polish, low flow caused by cardiac bypass, hypotension, vasoconstriction, and the like.

In monitoring one's health there is a constant need to know how many calories have been expended whether exercising or going about one's daily routine. A calorie is a measure of heat, generated when energy is produced in our bodies. The amount of calories burned during exercise is a measure of the total amount of energy used during a workout. This can be important, since increased energy usage through exercise helps reduce body fat. There are several means to measure this expenditure of energy. To calculate the calories burned during exercise one multiplies the intensity level of the exercise by one's body weight (in kilograms). This provides the amount of calories burned in an hour. A unit of measurement called a MET is used to rate the intensity of an exercise. One MET is equal to the amount of energy expended at rest.

For example, the intensity of walking 3 miles per hour ("mph") is about 3.3 METS. At this speed, a person who weighs 132 pounds (60 kilograms) will burn about 200 calories per hour (60×3.3=198).

The computer controls in higher-quality exercise equipment can provide a calculation of how many calories are burned by an individual using the equipment. Based on the workload, the computer controls of the equipment calculate exercise intensity and calories burned according to established formulae.

The readings provided by equipment are only accurate if one is able to input one's body weight. If the machine does not allow this, then the "calories per hour" or "calories used" displays are only approximations. The machines have built-in standard weights (usually 174 pounds) that are used when there is no specific user weight. There are devices that utilize a watch-type monitor to provide the wearer with heart rate as measured by a heartbeat sensor in a chest belt.

However, the prior art devices often suffer from noise, light and motion related problems. These problems are increased when the user participates in an athletic activity such as running. Further, attempting to correct one problem often creates additional problems such as increasing a sensor output which results in a shorter battery life. The prior art has failed to provide a means for monitoring one's health that is accurate, easy to wear on one's body for extended time periods, allows the user to input information and control the output, and provides sufficient information to the user about the user's health. Thus, there is a need for a monitoring device that can be worn for an extended period and provide health information to a user.

BRIEF SUMMARY OF THE INVENTION

The present invention provides a solution to the shortcomings of the prior art. The present invention is accurate, comfortable to wear by a user for extended time periods, allows for input and controlled output by the user, is light weight, and provides sufficient real-time information to the user about the user's health.

One aspect of the present invention is a method for monitoring a real-time vital sign of a user by using a signal from an optical sensor and a signal from a multiple axis accelerometer that generates an X-axis signal, a Y-axis signal and a Z-axis signal.

Another aspect of the present invention is of the present invention is a system for monitoring a real-time vital sign of a user. The system for monitoring a real-time vital sign of a user comprises a monitoring device comprising an optical sensor for generating a real-time digitized optical signal corresponding to a flow of blood through an artery of the user and an accelerometer for generating real-time accelerometer data comprising a X-axis signal, a Y-axis signal and a Z-axis signal based on a movement of the user. The system further comprises a first transceiver for transmitting the real-time digitized optical signal and the real-time accelerometer data from the monitoring device. Additionally, the system comprises a mobile communication device comprising a second transceiver for receiving the real-time digitized optical signal and the real-time accelerometer data from the monitoring device. Additionally, the system comprises a processor in electrical communication with the second transceiver, the processor configured to receive the real-time digitized signal and the real-time accelerometer data, the processor configured to calculate a period of motion related harmonics from the real-time accelerometer data utilizing a repetitive motion pattern analyzer, the processor configured to modify the real-time digitized optical signal by suppressing the motion related harmonics calculated by the motion pattern analyzer to generate a modified optical signal, the processor configured to generate a real-time heart rate for the user from the modified optical signal, Optionally, the modified optical signal is filtered with a narrow band filter adaptively tuned to a heart rate frequency calculated by a heart rate evaluator to generate the real-time heart rate for the user. Preferably, the repetitive motion pattern analyzer comprises an array of Comb filters. Preferably, the optical sensor comprises two green LEDs and a photodetector.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
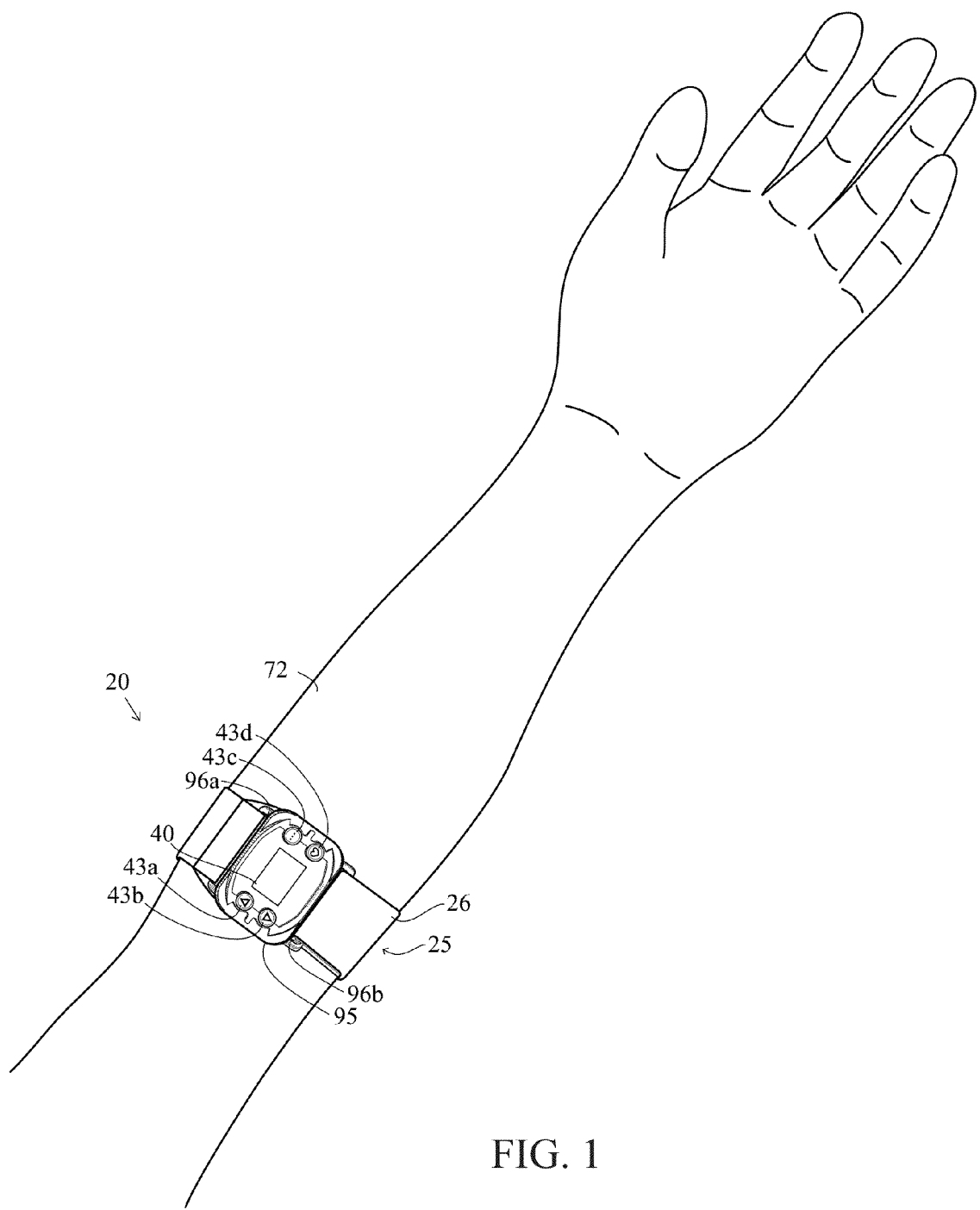
FIG. 1 is a plan view of a preferred embodiment of a monitoring device worn by a user.
Figure 2:
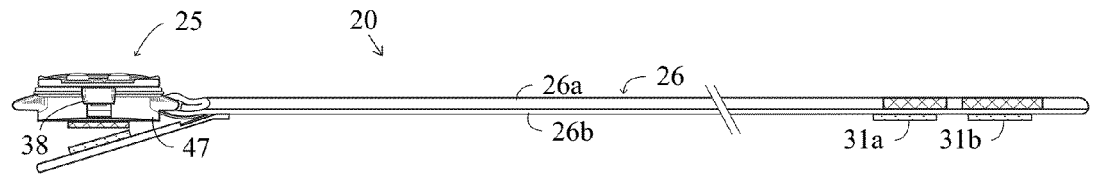
FIG. 2 is a side view of a monitoring device.
Figure 3:
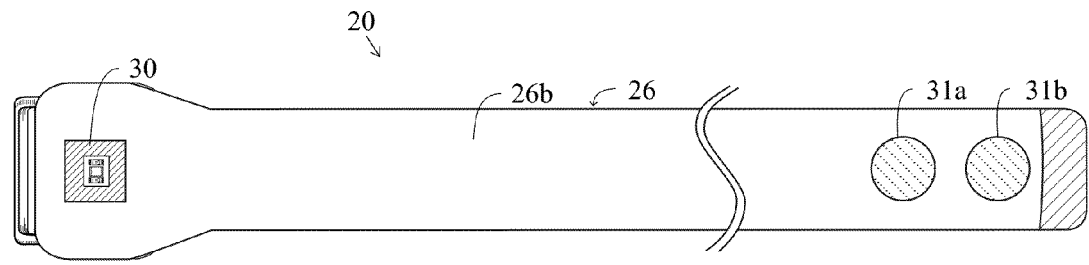
FIG. 3 is an interior surface plan view of a monitoring device.
Figure 4:
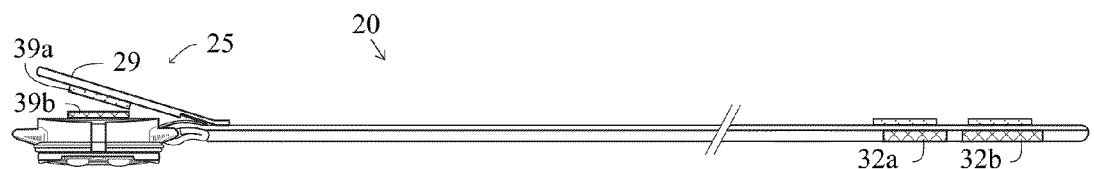
FIG. 4 is a side view of a monitoring device.

As shown in FIGS. 1-5, a monitoring device is generally designated 20. The monitoring device 20 preferably includes an article 25 and an attachment band 26 having an exterior surface 26a and interior surface 26b. The monitoring device 20 is preferably secured with VELCRO® hook and loop material 31a and 31b. The article 25 preferably includes an optical sensor 30, control components 43a-43c and optionally a display member 40. The monitoring device 20 is preferably worn on a user's wrist, arm or ankle.

The article 25 preferably has a USB port for a wired connection to a computer, tablet, video monitor or mobile communication device such as smartphone.

It is desirous to adapt the monitoring device 20 to the anatomy of the user's arm or even the user's ankle. The band 26 is preferably composed of neoprene, leather, synthetic leather, LYCRA, another similar material, or a combination thereof. The article 25 is preferably composed of a semi-rigid or rigid plastic with a rubber-like or semi-flex plastic bottom layer for contact with the user's body. The bottom layer of the article 25 may have a curve surface for contact with a user's body. The article 25 preferably has a mass ranging from 5 grams to 50 grams. Preferably, the lower the mass of the article 25, the more comfort to the user. The article 25 preferably has a thickness ranging from 5 mm to 10 mm, and is most preferably 6.5 mm.

Although the monitoring device 20 is described in reference to an article worn on a user's arm, wrist or ankle, those skilled in the pertinent art will recognize that the monitoring device 20 may take other forms such as eyewear disclosed in Brady et al, U.S. Pat. No. 7,648,463, for a Monitoring Device, Method And System, which is hereby incorporated by reference in its entirety or a glove such as disclosed in Rulkov et al., U.S. Pat. No. 7,887,492, for a Monitoring Device, Method And System, which is hereby incorporated by reference in its entirety.

The optical sensor 30 of the monitoring device 20 is preferably positioned over the radial artery or ulnar artery if the article 25 is worn on the user's arm. The optical sensor 30 of the monitoring device 20 is preferably positioned over the posterior tibial artery of a user if the article 25 is worn on the user's ankle. However, those skilled in the pertinent art will recognize that the optical sensor may be placed over other arteries of the user without departing from the scope and spirit of the present invention. Further, the optical sensor 30 need only be in proximity to an artery of the user in order to obtain a reading or signal.

In a preferred embodiment, the optical sensor 30 is a plurality of light emitting diodes ("LED") 35 based on green light wherein the LEDs 35 generate green light (wavelength of 500-570 nm), and a photodetector 36 detects the green light. Yet in an alternative embodiment, the optical sensor 30 is a photodetector 36 and a single LED 35 transmitting light at a wavelength of approximately 900 nanometers as a pulsed infrared LED. Yet further, the optical sensor is a combination of a green light LED and a pulsed infrared LED to offset noise affects of ambient light and sunlight. As the heart pumps blood through the arteries in the user's arm, ankle or wrist, the photodetector 36, which is typically a photodiode, detects reflectance/transmission at the wavelengths (green, red or infrared), and in response generates a radiation-induced signal.

A preferred optical sensor 30 utilizing green light is a TRS1755 sensor from TAOS, Inc of Plano Tex. The TRS1755 comprises a green LED light source (567 nm wavelength) and a light-to-voltage converter. The output voltage is directly proportional to the reflected light intensity. Another preferred photodetector 36 is a light-to-voltage photodetector such as the TSL260R and TSL261, TSL261R photodetectors available from TAOS, Inc of Plano Tex. Alternatively, the photodetector 130 is a light-to-frequency photodetector such as the TSL245R, which is also available from TAOS, Inc. The light-to-voltage photodetectors have an integrated transimpedance amplifier on a single monolithic integrated circuit, which reduces the need for ambient light filtering. The TSL261 photodetector preferably operates at a wavelength greater than 750 nanometers, and optimally at 940 nanometers, which would preferably have a LED that radiates light at those wavelengths.

In one embodiment, discussed below, the display member 40 is removed and the signal is sent to a device such as a personal digital assistant, laptop computer, mobile telephone, exercise equipment, or the like for display and even processing of the user's real-time vital signs information. Alternatively, the circuitry assembly includes a flexible microprocessor board which is a low power, micro-size easily integrated board which provides blood oxygenation level, pulse rate (heart rate), signal strength bargraph, plethysmogram and status bits data. The microprocessor can also store data. The microprocessor can process the data to display pulse rate, blood oxygenation levels, calories expended by the user of a pre-set time period, target zone activity, time and dynamic blood pressure. Further, microprocessor preferably includes an automatic gain control for preventing saturation of the photodetector, which allows for the device to be used on different portions of the human body.

The display member 40 is preferably a light emitting diode ("LED"). Alternatively, the display member 40 is a liquid crystal display ("LCD") or other similar display device.

A microprocessor processes the signal generated from the optical sensor 30 to generate the plurality of vital sign information for the user which is displayed on the display member 40. The control components 43a-c are connected to the processor to control the input of information and the output of information displayed on the display member 40.

The monitoring device 20 is preferably powered by a power source positioned on the article 25. Preferably the power source is a battery. The power source 360 is preferably an AA or AAA disposable or rechargeable battery. The power source is alternatively a lithium ion rechargeable battery such as available from NEC-Tokin. The power source preferably has an accessible port for recharging. The circuit assembly of the monitoring device preferably requires 5 volts and draws a current of 20-to 40 milliamps. The power source preferably provides at least 900 milliamp hours of power to the monitoring device 20.

Figure 6:
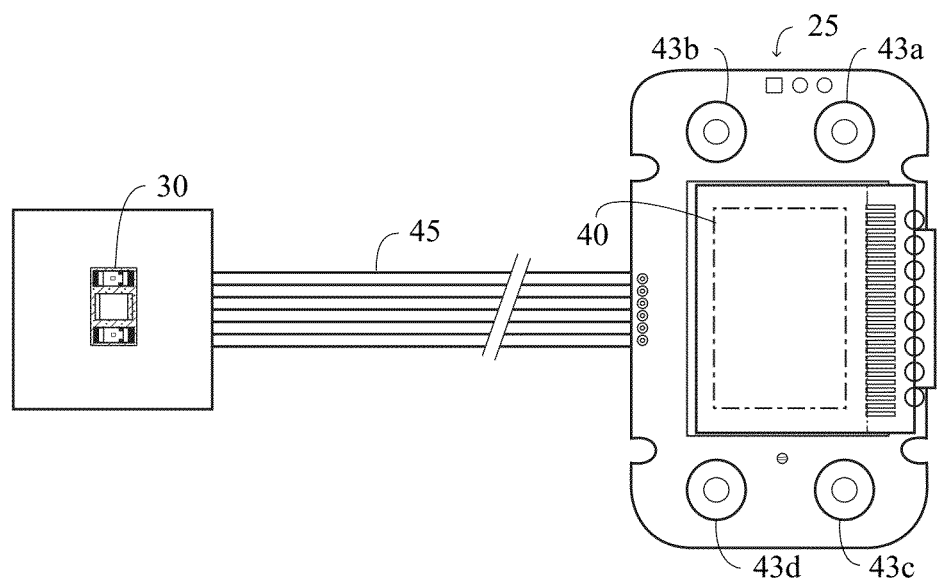
FIG. 6 is an isolated view of the electrical components of a monitoring device.
Figure 7:
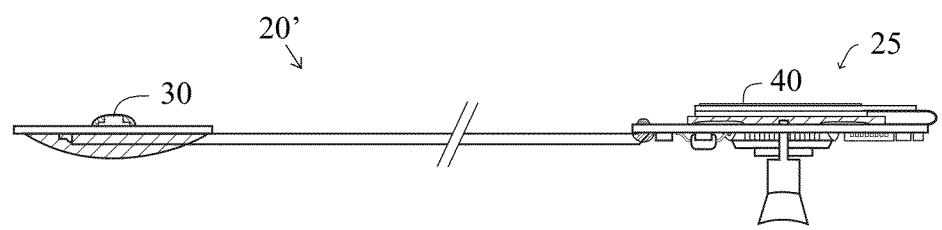
FIG. 7 is isolated side view of the electrical components of a monitoring device.
Figure 8:
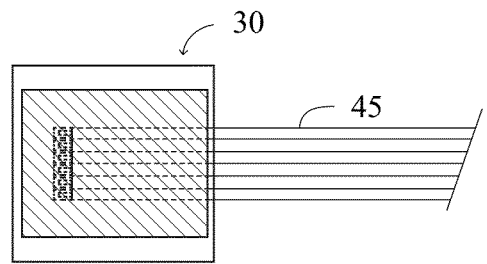
FIG. 8 is an isolated exterior surface view of an optical sensor for a monitoring device.

A connection wire arrangement 45 is shown in FIGS. 6 and 8, wherein the connection 45 between the microprocessor and the optical sensor 30 is preferably non-planar or non-straight in order to reduce noise in the signal. The optical sensor 30 preferably comprises a photodetector 36, and first and second LEDs 35 which transmit light. Using two LEDs on each side of a photodetector creates a more mechanically stable optical sensor 30.

The monitoring device 20 alternatively has a short-range wireless transceiver which is preferably a transmitter operating on a wireless protocol, e.g. BLUETOOTH, part-15, or 802.11. "Part-15" refers to a conventional low-power, short-range wireless protocol, such as that used in cordless telephones. Other communication protocols include a part 15 low power short range radio, standard BLUETOOTH or BLUETOOTH Low Energy to conserve power or other low power short range communications means. The short-range wireless transmitter (e.g., a BLUETOOTH transmitter) receives information from the microprocessor and transmits this information in the form of a packet through an antenna. An external laptop computer or hand-held device features a similar antenna coupled to a matched wireless, short-range receiver that receives the packet. In certain embodiments, the hand-held device is a cellular telephone with a Bluetooth circuit integrated directly into a chipset used in the cellular telephone. In this case, the cellular telephone may include a software application that receives, processes, and displays the information. The secondary wireless component may also include a long-range wireless transmitter that transmits information over a terrestrial, satellite, or 802.11-based wireless network. Suitable networks include those operating at least one of the following protocols: CDMA, GSM, GPRS, Mobitex, DataTac, iDEN, and analogs and derivatives thereof. Alternatively, the handheld device is a pager or PDA.

A general method is as follows. The light source 35 transmits light through at least one artery of the user. The photodetector 36 detects the light. The pulse rate is determined by the signals received by the photo-detector 36.

This information is sent to the microprocessor for creation of user's real-time pulse rate. The microprocessor further processes the information to display pulse rate, calories expended by the user of a pre-set time period, target zones of activity, time and/or dynamic blood pressure. The information is displayed on a display member or electro-optical display.

Figure 5:
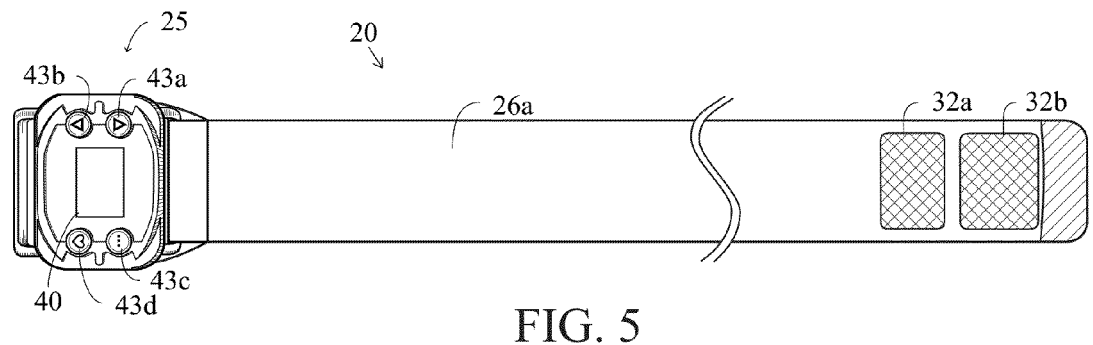
FIG. 5 is an exterior surface view of a monitoring device.

In a preferred embodiment, the article 25 has four control buttons 43a-d as shown in FIGS. 1 and 5. The control buttons 43a-d are preferably positioned in relation to the display member 40 to allow the user immediate visual feedback of the user's inputted information. The middle control button 43b preferably activates and deactivates the article 25. The left button 43a is preferably used to scroll through the different modes. The right button 43c is preferably used to input data. The control buttons 43a-d allow for the user's personal data to be entered and for choices to be selected by the user. The left button 43a preferably allows for the user's calories burned to be displayed on the display member 40 and for the activity to be reset, and allows for other fitness monitoring features to be displayed.

To activate the article 25, the middle button 43b is depressed for preferably 0.5 seconds and then released. The display member will appear with a current pulse of the user and a calories burned display. The microprocessor preferably stores the calories burned and accumulates the values for a daily calories burned value and a total calories burned value until the activity is reset.

To enter the user's personal data, the middle button 43b is depressed for 2 seconds and then released. The user will enter gender, age, mass, height and resting heart rate. Entering the data entails pushing the middle button to select a category (gender, age, . . . ) and then pushing the right or left button to scroll through the available options or to enter a value (e.g. age of the user). The middle button 43b is pressed again to save the entry. This process is preformed until the user's has entered all of the data that the user wishes to enter into the microprocessor. The display member 40 will then display a heart rate and current calories burned value. A preset resting heart rate for men and women is preferably stored on the microprocessor, and used as a default resting heart rate. However, the user may enter their own resting heart rate value if the user is aware of that value. To access daily calories, the left button 43a is pushed by the user and the display member 40 will illustrate the value for daily calories burned by the user. If the left button 43a is pushed again, the value for total calories burned by the user will be displayed on the display member 40. The left button 43a is pushed again to return to a heart rate value on the display member 40.

The right button 43c is pushed to scroll through the choices of other output values, which comprises: basal metabolic rate; average heart rate; minimum heart rate; maximum heart rate; fat burn heart rate exercise target zone; cardio burn heart rate exercise target zone; and, summary of daily calories burned. The basal metabolic rate (displayed as "BMR") is an estimate of the total calories burned by the user in one day without exercise, and is based on the user inputted personal data. The average heart rate (displayed as "avHR") is the average heart rate of the user between resets, and is an overall indicator of fitness. The lower the average heart rate, the healthier the heart. The average heart rate is also a measure of the effectiveness of the exercise program employed by the user since a decrease in the average heart rate of the user will indicate the user's fitness has improved. The minimum heart rate (displayed as "mnHR") of the user is typically measured during sleep and periods of relaxation. The maximum heart rate (displayed as "mxHR") is typically measured during intense workouts. The fat burn heart rate exercise target zone (displayed as "fatB") displays a low and high range for the heart rate of the user to optimize fat burning during exercise. The cardio burn heart rate exercise target zone provides a high and low range for the heart rate of the user to optimize cardio conditioning during exercise. The summary of daily calories burned (displayed as "cal") displays the daily calories burned by the user.

In a preferred embodiment, the accelerometer is a multiple-axis accelerometer, such as the ADXL202 made by Analog Devices of Norwood, Mass. This device is a standard microelectronic-machine ("MEMs") module that measures acceleration and deceleration using an array of silicon-based structures.

In yet another embodiment, the monitoring device 20 comprises a first thermistor, not shown, for measuring the temperature of the user's skin and a second thermistor, not shown, for measuring the temperature of the air. The temperature readings are displayed on the display member 40 and the skin temperature is preferably utilized in further determining the calories expended by the user during a set time period. One such commercially available thermistor is sold under the brand LM34 from National Semiconductor of Santa Clara, Calif. A microcontroller that is utilized with the thermistor is sold under the brand name ATMega 8535 by Atmel of San Jose, Calif.

The monitoring device 20 may also be able to download the information to a computer for further processing and storage of information. The download may be wireless or through cable connection. The information can generate an activity log or a calorie chart.

The microprocessor can use various methods to calculate calories burned by a user. One such method uses the Harris-Benedict formula. The Harris-Benedict formula uses the factors of height, weight, age, and sex to determine basal metabolic rate (BMR). This equation is very accurate in all but the extremely muscular (will underestimate calorie needs) and the extremely overweight (will overestimate caloric needs) user.

The equations for men and women are set forth below:

$$\text{Men: BMR} = 66 + (13.7 \times \text{mass(kg)}) + (5 \times \text{height(cm)}) - (6.8 \times \text{age (years)})$$

$$\text{Women: BMR} = 655 + (9.6 \times \text{mass}) + (1.8 \times \text{height}) - (4.7 \times \text{age})$$

The calories burned are calculated by multiplying the BMR by the following appropriate activity factor: sedentary; lightly active; moderately active; very active; and extra active.

Sedentary=BMR multiplied by 1.2 (little or no exercise, desk job)

Lightly active=BMR multiplied by 1.375 (light exercise/sports 1-3 days/wk)

Moderately Active=BMR multiplied by 1.55 (moderate exercise/sports 3-5 days/wk)

Very active=BMR multiplied by 1.725 (hard exercise/sports 6-7 days/wk)

Extra Active=BMR multiplied by 1.9 (hard daily exercise/sports & physical job or 2× day training, marathon, football camp, contest, etc.)

Various target zones may also be calculated by the microprocessor. These target zones include: fat burn zone; cardio zone; moderate activity zone; weight management zone; aerobic zone; anaerobic threshold zone; and red-line zone.

$$\text{Fat Burn Zone} = (220 - \text{age}) \times 60\% \ \& \ 70\%$$

An example for a thirty-eight year old female:
i. (220−38)×0.6=109
ii. (220−38)×0.7=127
iii. Fat Burn Zone between 109 to 127 heart beats per minute.

$$\text{Cardio Zone} = (220 - \text{your age}) \times 70\% \ \& \ 80\%$$

An example for a thirty-eight year old female:
i. (220−38)×0.7=127
ii. (220−38)×0.8=146 iii. Cardio zone is between 127 & 146 heart beats per minute.

Moderate Activity Zone, at 50 to 60 percent of your maximum heart rate, burns fat more readily than carbohydrates. That is the zone one should exercise at if one wants slow, even conditioning with little pain or strain.

Weight Management Zone, at 60 to 70 percent of maximum, strengthens ones heart and burns sufficient calories to lower one's body weight.

Aerobic Zone, at 70 to 80 percent of maximum, not only strengthens one's heart but also trains one's body to process oxygen more efficiently, improving endurance.

Anaerobic Threshold Zone, at 80 to 90 percent of maximum, improves one's ability to rid one's body of the lactic-acid buildup that leads to muscles ache near one's performance limit. Over time, training in this zone will raise one's limit.

Red-Line Zone, at 90 to 100 percent of maximum, is where serious athletes train when they are striving for speed instead of endurance.

Example One

Female, 30 yrs old, height 167.6 centimeters, weight 54.5 kilograms.

The BMR=655+523+302−141=1339 calories/day.

The BMR is 1339 calories per day. The activity level is moderately active (work out 3-4 times per week). The activity factor is 1.55. The TDEE=1.55×1339=2075 calories/day. TDEE is calculated by multiplying the BMR of the user by the activity multiplier of the user.

The heart rate may be used to dynamically determine an activity level and periodically recalculate the calories burned based upon that factor. An example of such an activity level look up table might be as follows:

Activity/Intensity Multiplier Based on Heart Rate

Sedentary=BMR×1.2 (little or no exercise, average heart rate 65-75 bpm or lower)

Lightly active=BMR×3.5 (light exercise, 75 bpm–115 bpm)

Mod. active=BMR×5.75 (moderate exercise, 115-140 pm)

Very active=BMR×9.25 (hard exercise, 140-175 bpm)

Extra active=BMR×13 (175 bpm–maximum heart rate as calculated with MHR formula)

For example, while sitting at a desk, a man in the above example might have a heart rate of between 65 and 75 beats per minute (BPM). (The average heart rate for an adult is between 65 and 75 beats per minute.) Based on this dynamically updated heart rate his activity level might be considered sedentary. If the heart rate remained in this range for 30 minutes, based on the Harris-Benedict formula he would have expended 1.34 calories a minute×1.2 (activity level)×30 minutes, which is equal to 48.24 calories burned.

If the man were to run a mile for 30 minutes, with a heart rate ranging between 120 and 130 bpm, his activity level might be considered very active. His caloric expenditure would be 1.34 calories a minute×9.25 (activity level)×30 minutes, which is equal to 371.85.

Another equation is weight multiplied by time multiplied by an activity factor multiplied by 0.000119.

Figure 10:
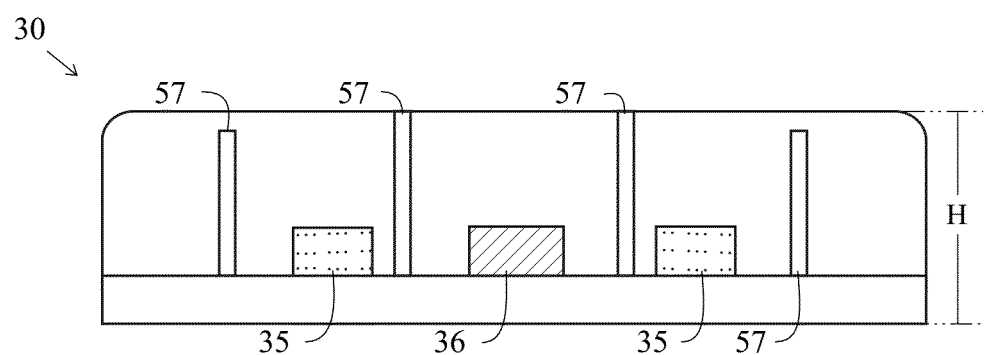
FIG. 10 is an isolated cross section view of an optical sensor for a monitoring device.
Figure 13:
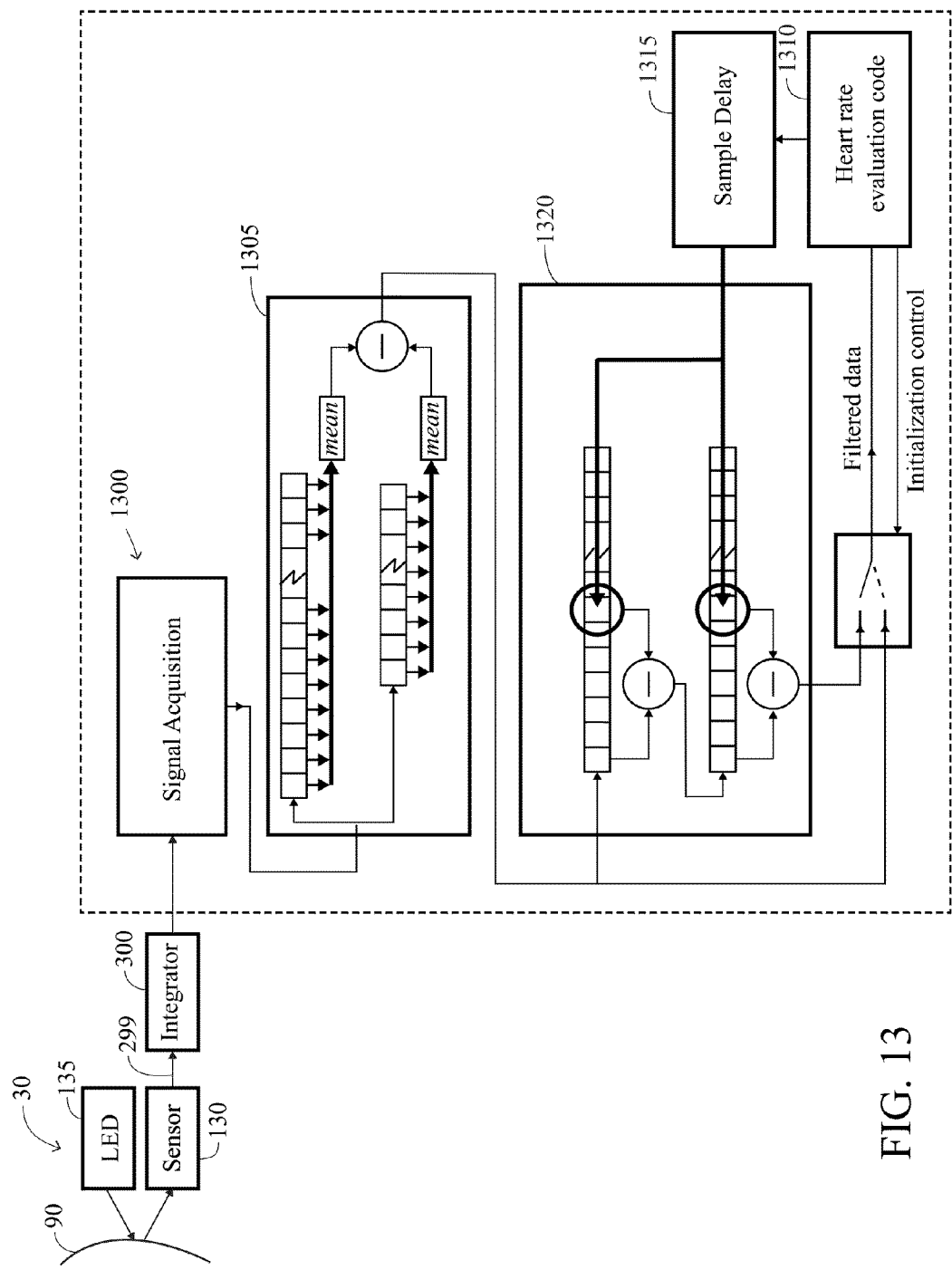
FIG. 13 is a block diagram of signal processing for a monitoring device.
Figure 14:
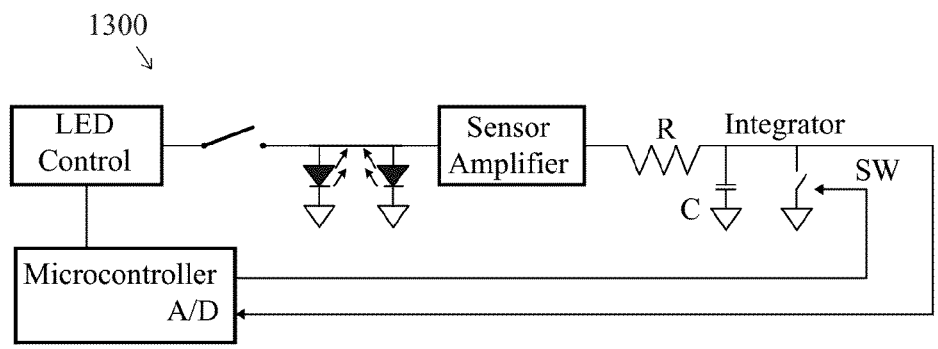
FIG. 14 is a schematic flow chart of the signal acquisition step of the flow chart of FIG. 13.
Figure 15:
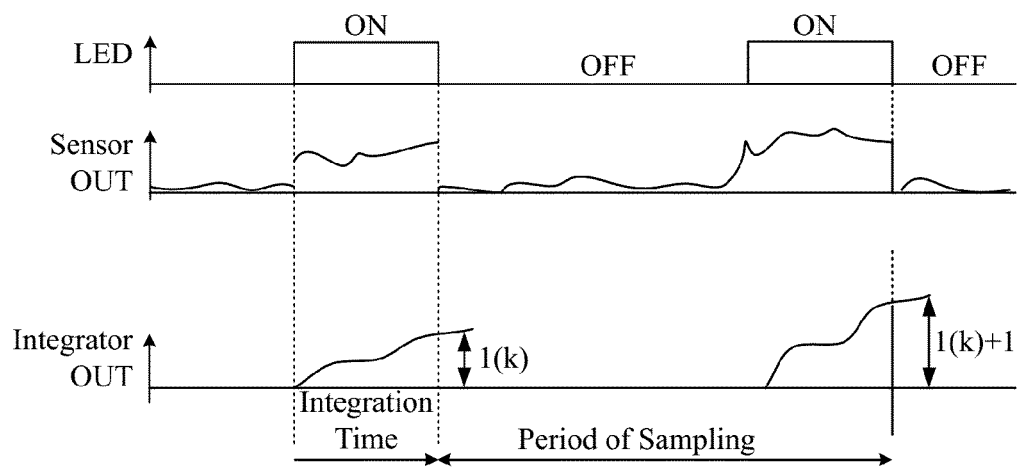
FIG. 15 is an illustration of the waveforms of the data sampling during the signal processing method.

FIG. 13 illustrates a block diagram of a flow chart of a signal processing method of the present invention. As shown in FIG. 10, the photodetector 36 of the optical sensor 30 receives light from the light source 35 while in proximity to the user's artery. The light source 35 is preferably a plurality of LEDs 35. The intensity of the light is preferably controlled by an integrator 300. In a preferred embodiment, the optical sensor 30 is a TRS1755 which includes a green LED light source (567 nm wavelength) and a light-to-voltage converter. The output voltage is directly proportional to the reflected light intensity. The signal 299 is sent to the microprocessor. At block 1300, the signal acquisition is performed. In reference to FIGS. 14 and 15, in the pulse mode the LED 35 is periodically activated for short intervals of time by a signal from the microcontroller. The reflected pulse of light is received by the sensor, with the generation of a voltage pulse having an amplitude proportional to the intensity of the reflected light. When the LED is activated, the switch, SW, is open by the action of the control signal from the microcontroller, and the capacitor, C, integrates the pulse generated from the sensor by charging through the resistor R. Immediately prior to deactivation of the LED, the analog-to-digital converter acquires the value of the voltage integrated across the capacitor, C. The analog-to-digital converter generates a data sample in digital form which is utilized by the microcontroller for evaluation of the heart rate the wearer. Subsequent to the sample being acquired by the analog-to-digital converter, the LED is deactivated and the capacitor, C, is shortcut by switch, SW, to reset the integrator, RC. A signal indicating sensor saturation is also sent to the microcontroller for light control of the LEDs. This states remains unchanged for a given time interval after which the process is repeated, which is illustrated in FIG. 15. The signals are shown in FIG. 15, with the raw sensor signal received from the sensor amplifier shown as varying between reflected light when the LEDs are on and an ambient light level when the LEDs are off. The filtered signal from the high pass filter ("HPF") is shown as the filtered sensor signal in FIG. 14. The integrator reset signal is shown as integrator out signal in FIG. 15, and the integrator reset signal in FIG. 14.

At block 1305, a band pass filter is implemented preferably with two sets of data from the analog-to-digital converter. At block 1305, an average of the values of data samples within each of a first set of samples is calculated by the microprocessor. For example, the values of data samples within forty-four samples are summed and then divided by forty-four to generate an average value for the first set of samples. Next, an average of the values of data samples within a second set of samples is calculated by the microprocessor. For example, the values of data samples within twenty-two samples are summed and then divided by twenty-two to generate an average value for the second set of samples. Preferably, the second set of samples is less than the first set of samples. Next, the average value of the second set of samples is subtracted from the average value for the first set of samples to generate a first filtered pulse data value.

At block 1310, the filtered pulse data value is processed using a heart rate evaluation code to generate a first heart rate value. In a preferred method, the heart rate evaluation code obtains the heart rate by calculating the distance between crossing points of the voltage through zero. Once the first heart rate value is known, then an adaptive resonant filter is utilized to generate a filtered second heart rate value by attenuating interference caused by motion artifacts. At block 1315, a sample delay is computed as the period of evaluated heart rate divided by two.

At block 1320, preferably a two cascade adaptive resonant filter generates a second filtered pulse data value which is processed at block 1310 using the heart rate evaluation code to generate a second heart rate value. Those skilled in the pertinent art will recognize that three, four, or more, cascade adaptive resonant filters may be utilized in generating the second filtered pulse data value. Essentially, the highest and lowest values are disregarded in calculating the filtered second heart rate value. Alternatively, a phase is established and any values outside of the phase are disregarded in calculating the second heart rate value. The filtering is preferably continued during the use of the monitor thereby further refining the heart rate value of the user.

A motion sensor 1100 is included to assist in identifying motion noise and filtering the noise from the signal sent by the sensor 30. The motion sensor 1100, such as an accelerometer, is integrated into the circuitry and software of the monitoring device 20. As the motion sensor detects an arm swinging, the noise component is utilized with the signal processing noise filtering techniques to provide additional filtering to remove the noise element and improve the accuracy of the monitoring device 20. More specifically, the signal from the optical sensor 30 is transmitted to the processor where a custom blood pressure filter 41$w$ processes the signal which is further processed at by custom adaptive filter 41$x$ before being sent to a heart beat tracking system 41$y$ and then transmitted to a heart rate beat output 41$z$. The heart rate beat output 41$z$ provides feedback to the custom adaptive filter 41$x$ which also receives input from the motion sensor 1100.

Figure 17:
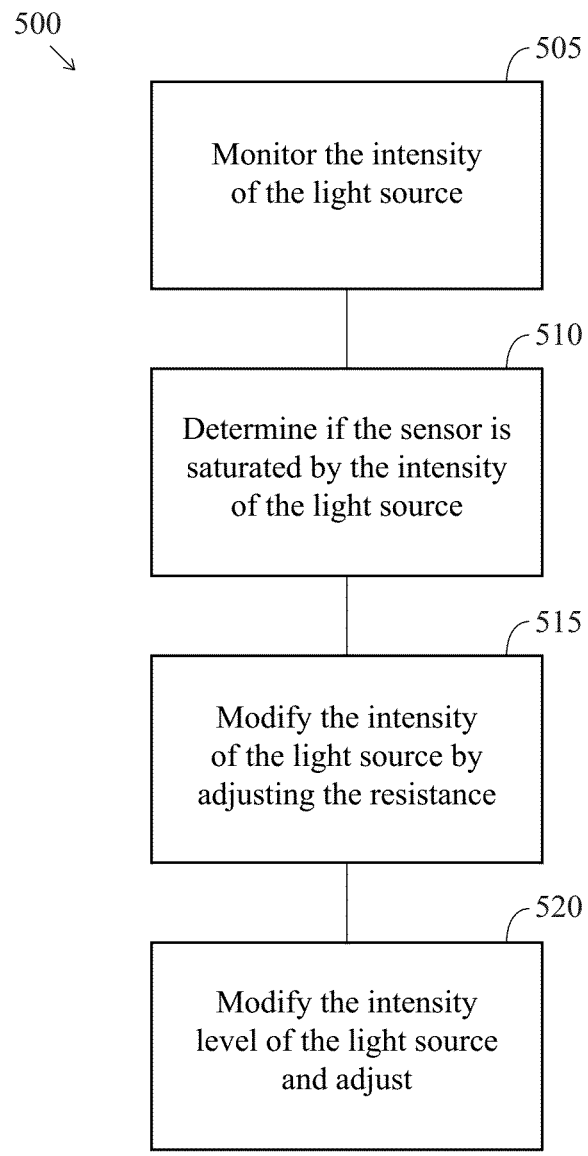
FIG. 17 is a flow chart of a signal processing method of the present invention.

FIG. 17 is a preferred method 500 for controlling the light intensity of the optical sensor 30. At block 505, the light intensity of the light source 35 is monitored. At block 510, the sensor/photodetector is determined to be saturated by the light source. At block 515, the intensity of the light source is modified by adjusting the resistance and the flow of current to the light source 35. At block 520, the light intensity is again monitored and adjusted if necessary. In a preferred embodiment, this automatic gain mechanism prevents the green light from overwhelming the photodetector 36 thereby maintaining an accurate reading no matter where the optical sensor is placed on the user.

Figure 16:
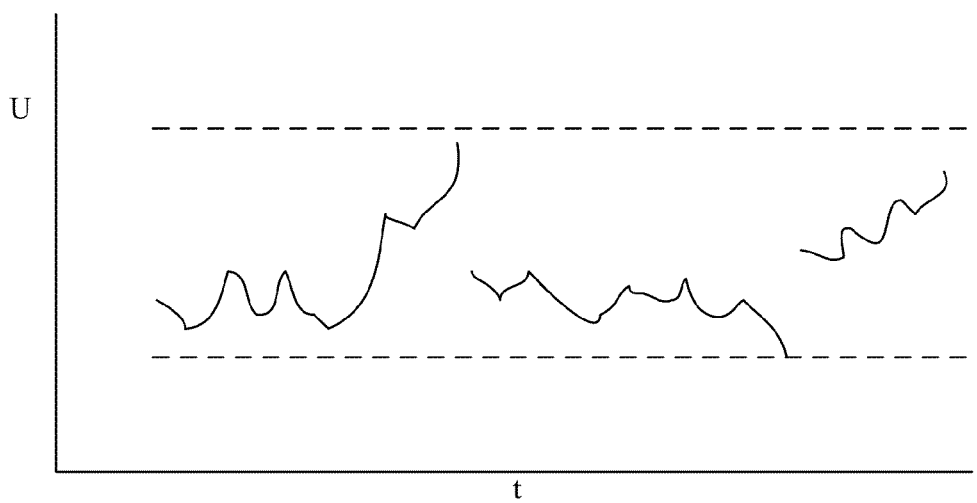
FIG. 16 is a graph illustrating the method and mechanism of controlling the intensity of the light source over time.

FIG. 16 illustrates how the control mechanism operates to maintain a proper light intensity. As the signal reaches the upper limit, the photodetector becomes saturated and the processor lowers the current flow, which results in a break in the signal. Then as the signal is lowered it becomes too low and the processor increases the light intensity resulting in a break in the signal.

Figure 18:
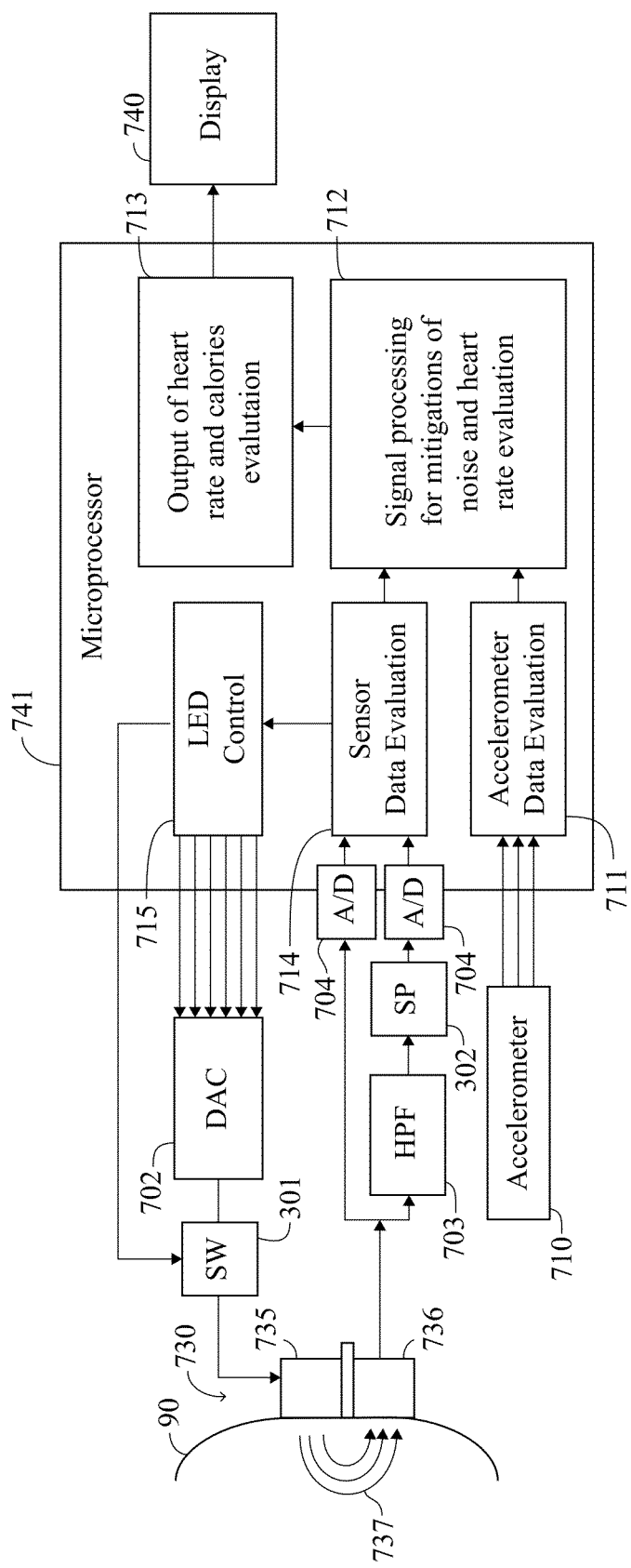
FIG. 18 is a block diagram of signal processing for a monitoring device.

A block diagram for vital sign signal processing is shown in FIG. 18. The optical sensor 730 is placed on or near an artery 90 of a user of the monitoring device 20. The optical sensor 730 has a pair of LEDs 735 and a photodetector 736, which receives reflected light 737 from the LEDs 735. The microprocessor 741 has a LED control 715 connected to DAC 702 for controlling the intensity of the LEDs 737. The signal from the photodetector 736 is transmitted to a high pass filter (HPF) 703 which sends it to an analog to digital converter 704, and the signal from the photodetector 737 is also sent directly to a second analog to digital converter 704. The real-time signal is then sent to a sensor data evaluation 714 to provide feedback to the LED control 715, and then is also sent to the filter of the signal processing for mitigations of noise and heart rate evaluations 712. Simultaneously, the accelerometer 710 transmits X-axis, Y-axis and Z-axis signals for the motion of the monitoring device 20 to an accelerometer data evaluation 711 of the microprocessor 741. This signal is then sent to the signal processing for mitigations of noise and heart rate evaluations 712. The output for the heart rate and/or calories is generated at block 713 of the microprocessor 741, which then sends the results to the display 740.

Figure 19:
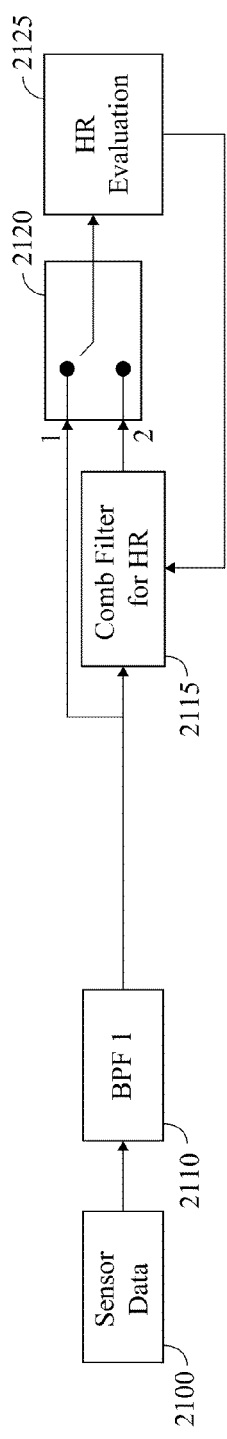
FIG. 19 is a block diagram of signal processing of a prior art device.

FIG. 19 illustrates a prior art signal processing of a vital sign without the use of an accelerometer to filter the signal. As shown in FIG. 19, sensor data at block 2100 is sent to a band pass filter 2110 and then to a comb filter 2115 and to a heart rate evaluator 2125 through a switch 2120. Feedback from the heart rate evaluator 2125 is sent to comb filter 2115, such as described in Brady et al., U.S. Pat. No. 7,468,036 for a Monitoring Device, Method And System, which is hereby incorporated by reference in its entirety.

Figure 20:
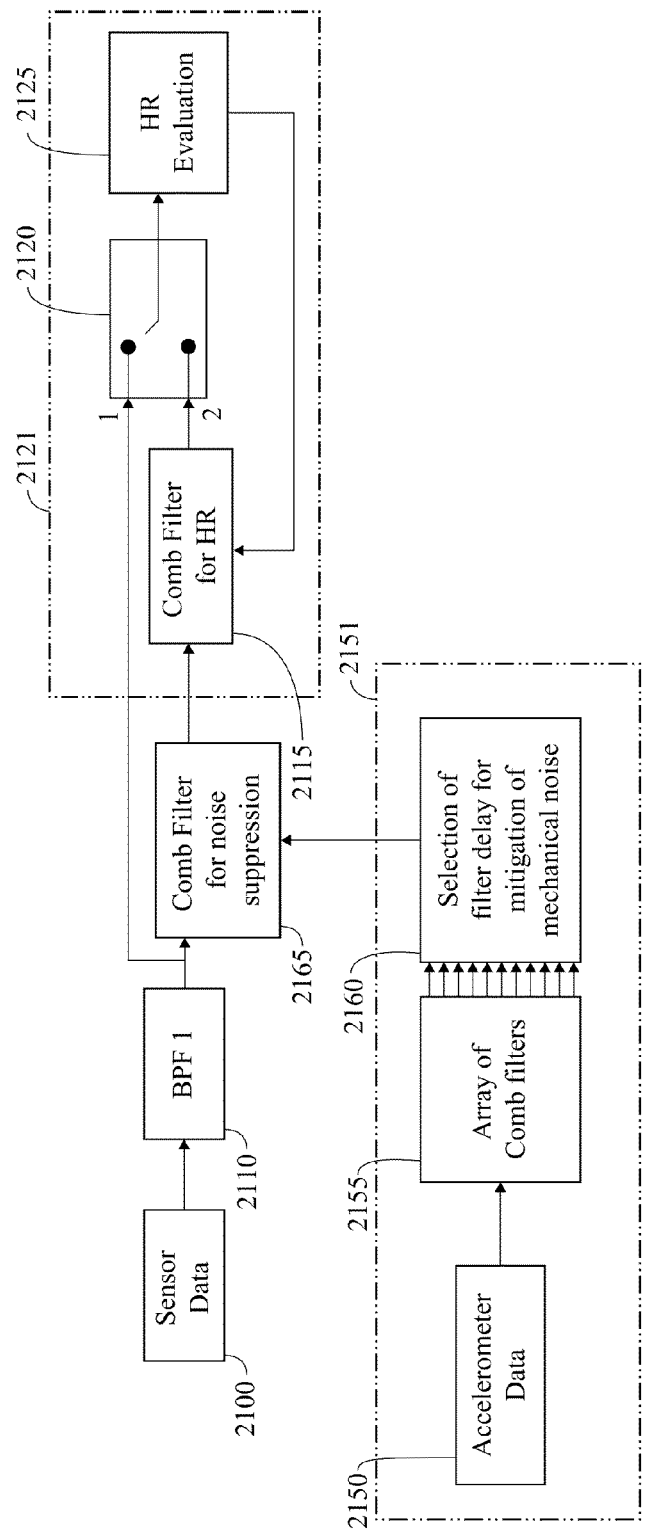
FIG. 20 is a block diagram of signal processing for a monitoring device.

FIG. 20 illustrates signal processing of a vital sign with the use of an accelerometer to filter the signal. As shown in FIG. 20, sensor data at block 2100 is sent to a band pass filter 2110 and then to a comb filter 2165 for noise suppression, then to a Comb filter for a heart rate 2215 and to a heart rate evaluator 2125 through a switch 2120. Feedback from the heart rate evaluator 2125 is sent to comb filter 2115. However, accelerometer data from block 2150 is sent to an array of Comb filters 2155, then to a selection of a filter delay for mitigation of mechanical noise at 2160 and then to comb filter 2165 for noise suppression in the vital sign signal from the vital sign sensor.

Figure 21:
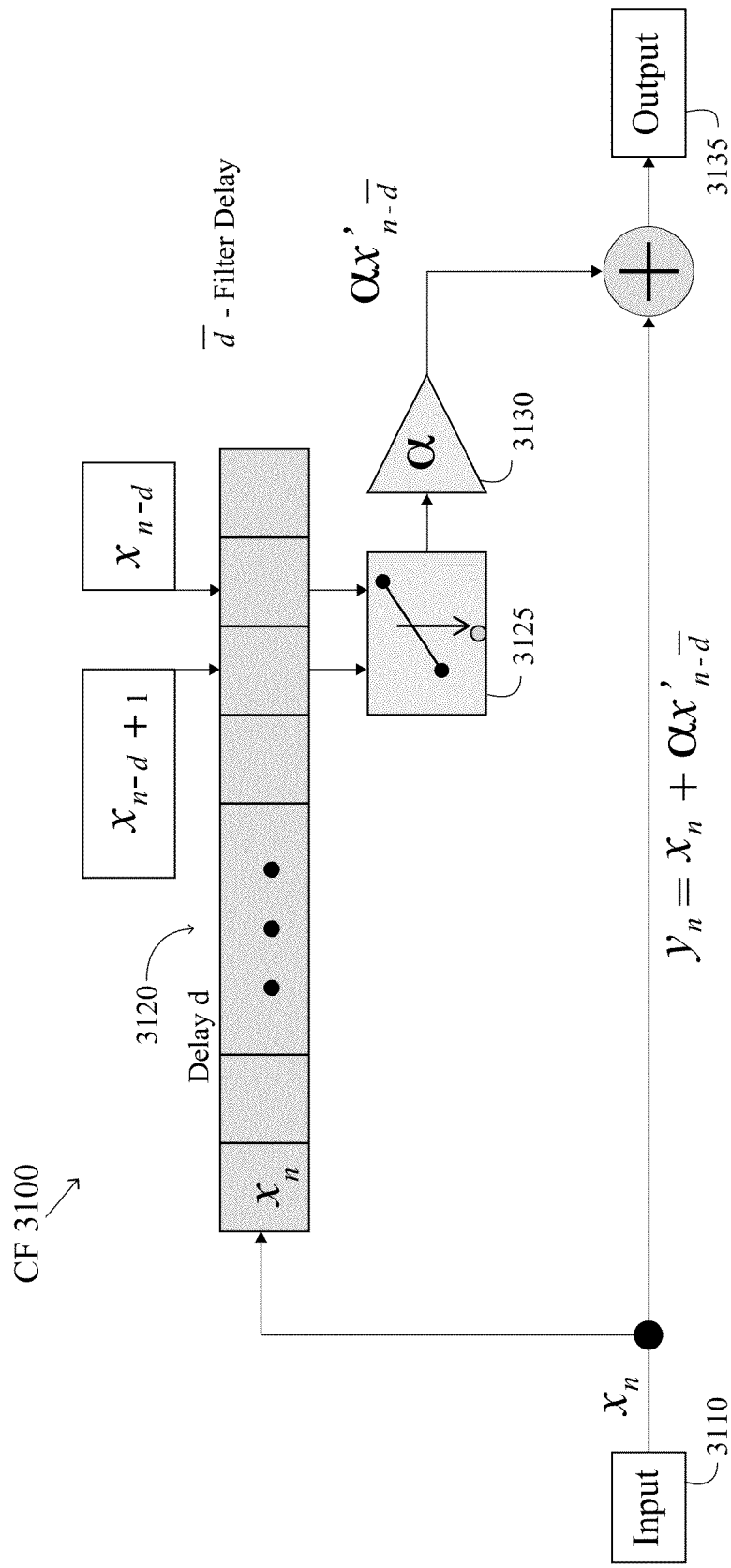
FIG. 21 is a block diagram of a comb filter type 2 for signal processing.

FIG. 21 illustrates a type 2 Comb filter 3100 which is preferably used as the Comb filter for noise suppression 2165 of FIG. 20. The signals begin at input 3110. A delay is generated at 3120, sent to interpolator 3125 and gain 3130 and then a filter delayed signal is sent from output 3135.

Figure 22:
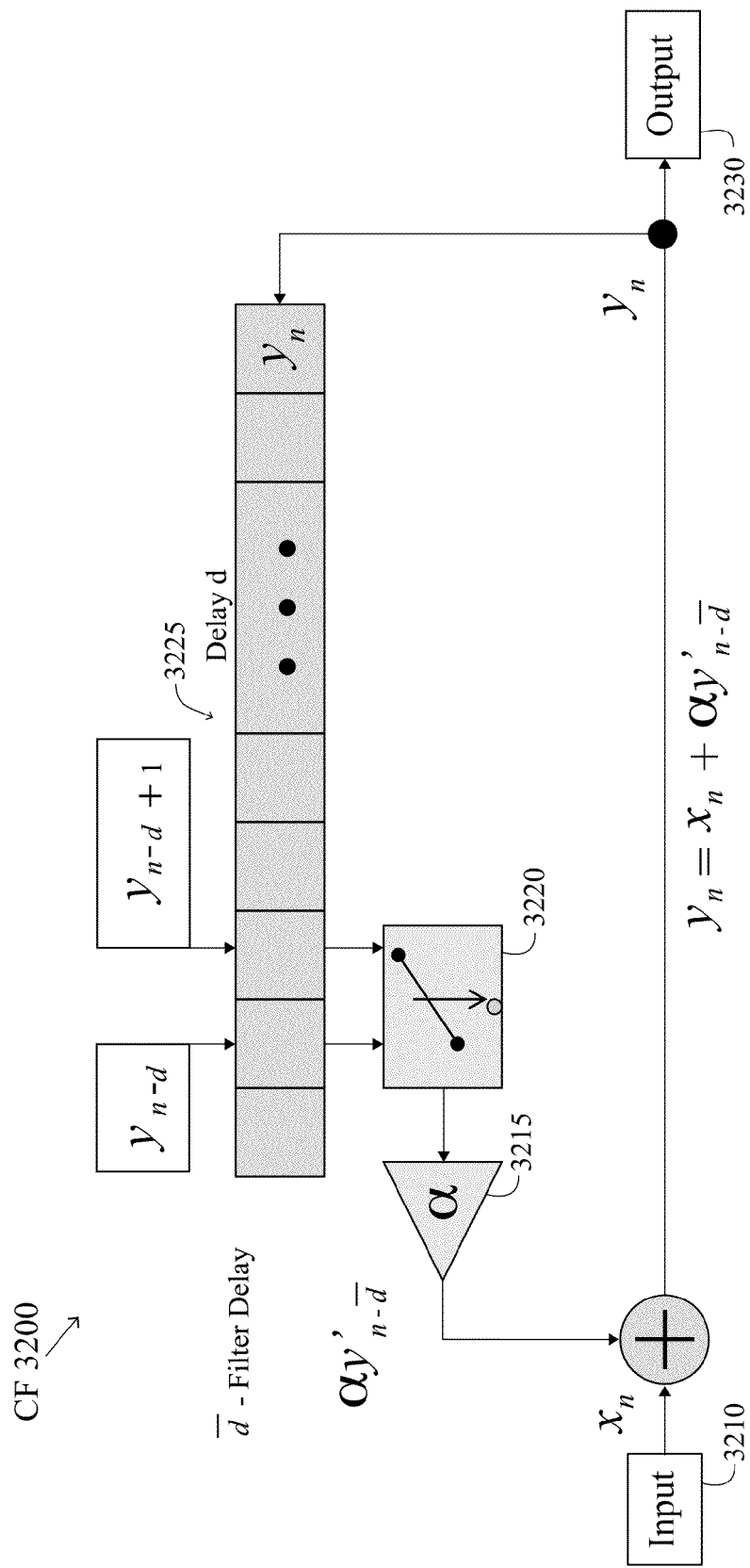
FIG. 22 is a block diagram of a comb filter type 1 for signal processing.

FIG. 22 illustrates a type 1 Comb filter 3200 which is preferably used as the Comb filter for the heart rate 2115 of FIG. 20. The signals begin at input 3210. A delay is generated at 3225, sent to interpolator 3220 and gain 3215 and then a filter delayed signal is sent from output 3230.

Figure 23:
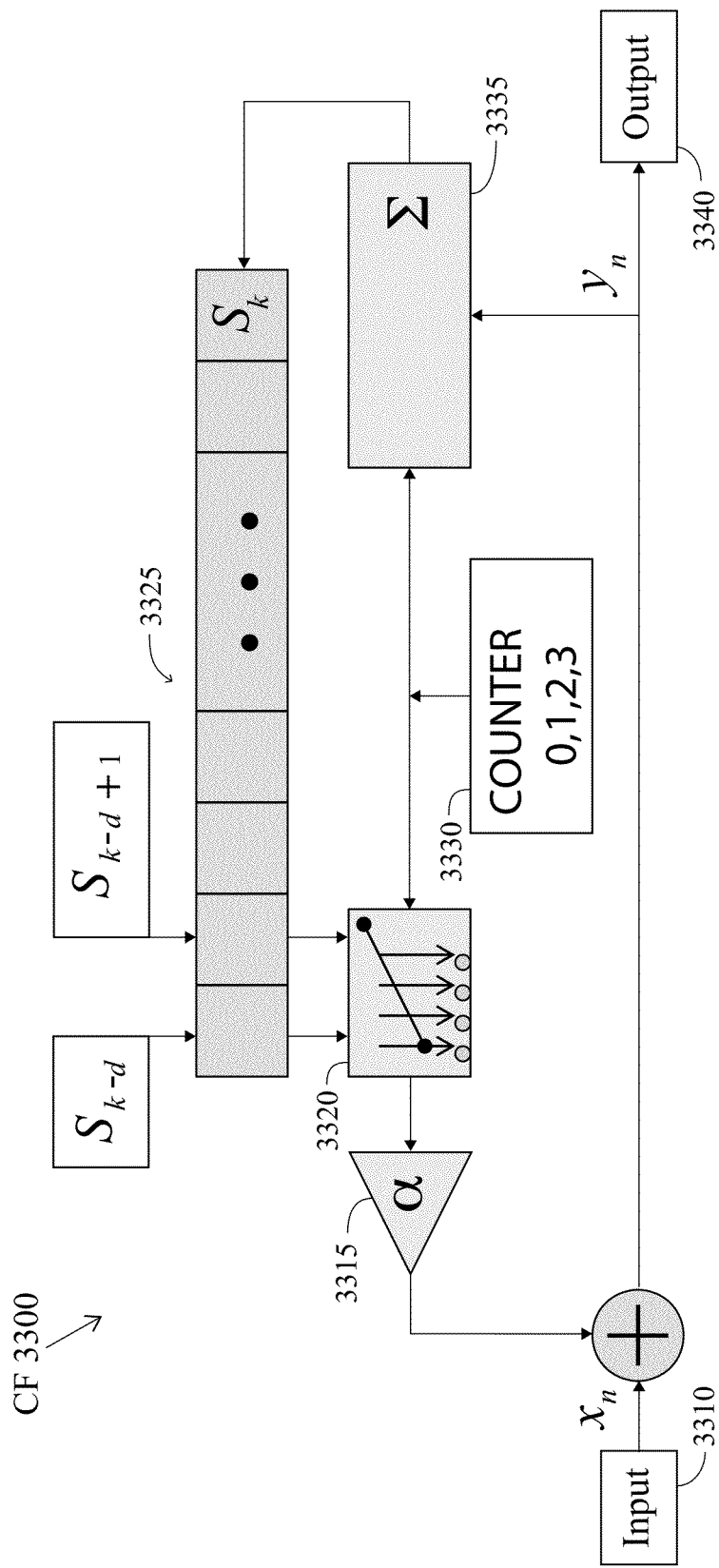
FIG. 23 is a block diagram of a four-cycle comb filter type 1 with a filter delay for signal processing.

FIG. 23 illustrates a four cycle Comb filter 3300 with a filter delay of 8, 12, 16, . . . , 4N, which is preferably used as at least one of the array of Comb filters 2155 of FIG. 20. The signals begin at input 3310. A collector 3335 sums the signals. A counter 3330 transmits signals to the collector and interpolator 3320. A delay is generated at 3325, sent to the interpolator 3320 and gain 3315 and then a filter delayed signal is sent from output 3340.

Figure 24:
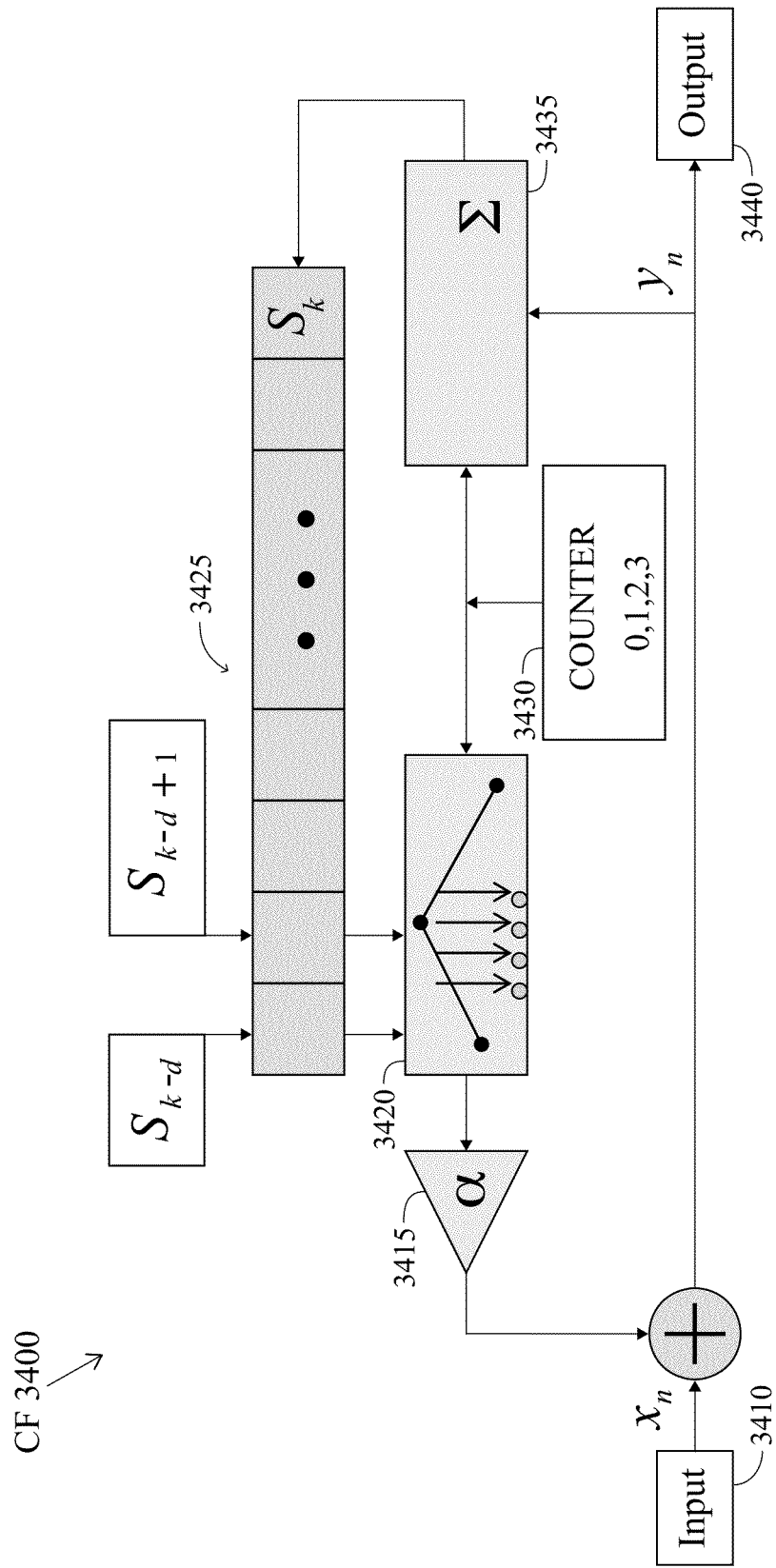
FIG. 24 is a block diagram of a four-cycle comb filter type 1 with a filter delay for signal processing.
Figure 25:
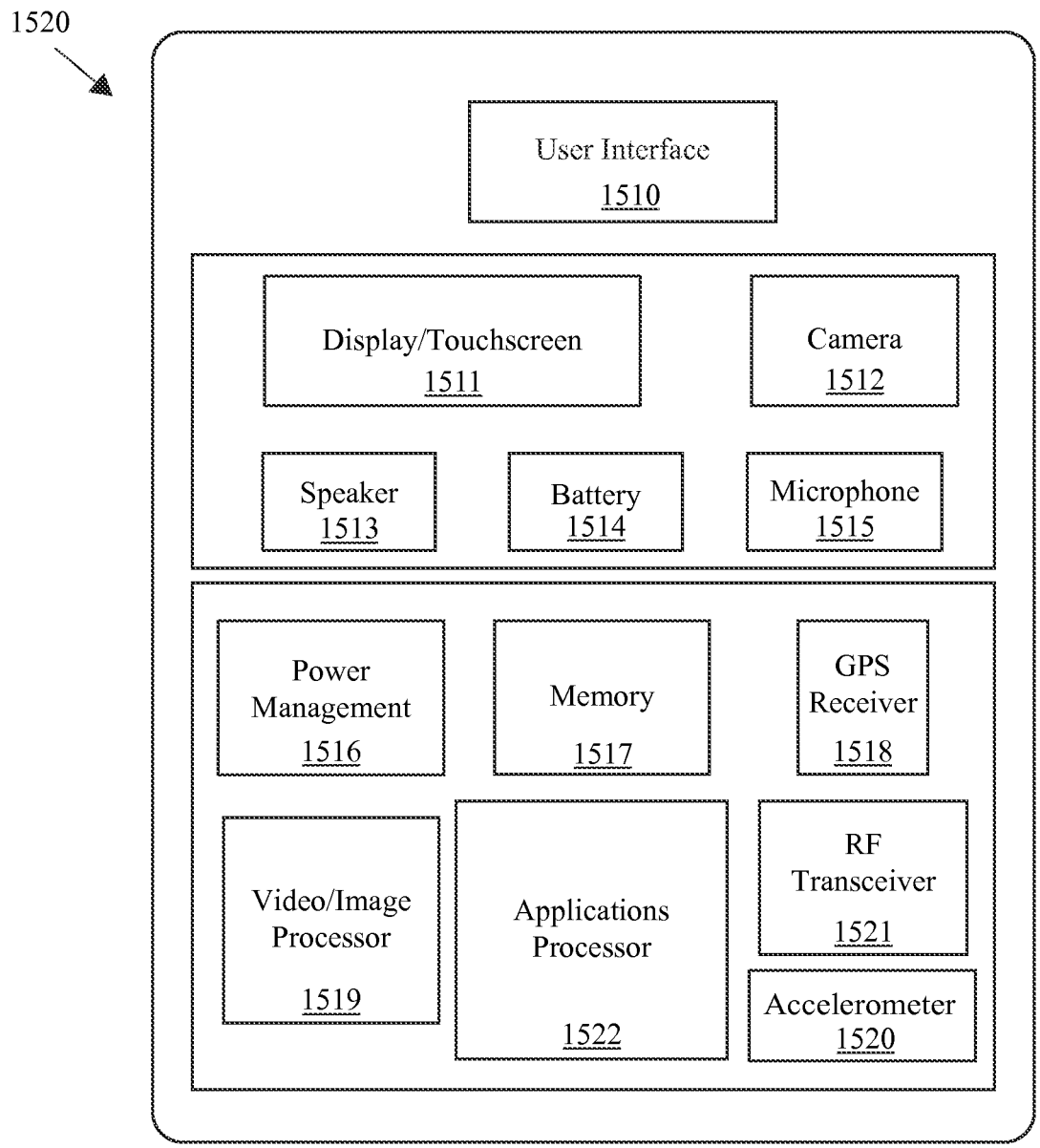
FIG. 25 is a block diagram of a mobile communication device such as a mobile phone.
Figure 26:
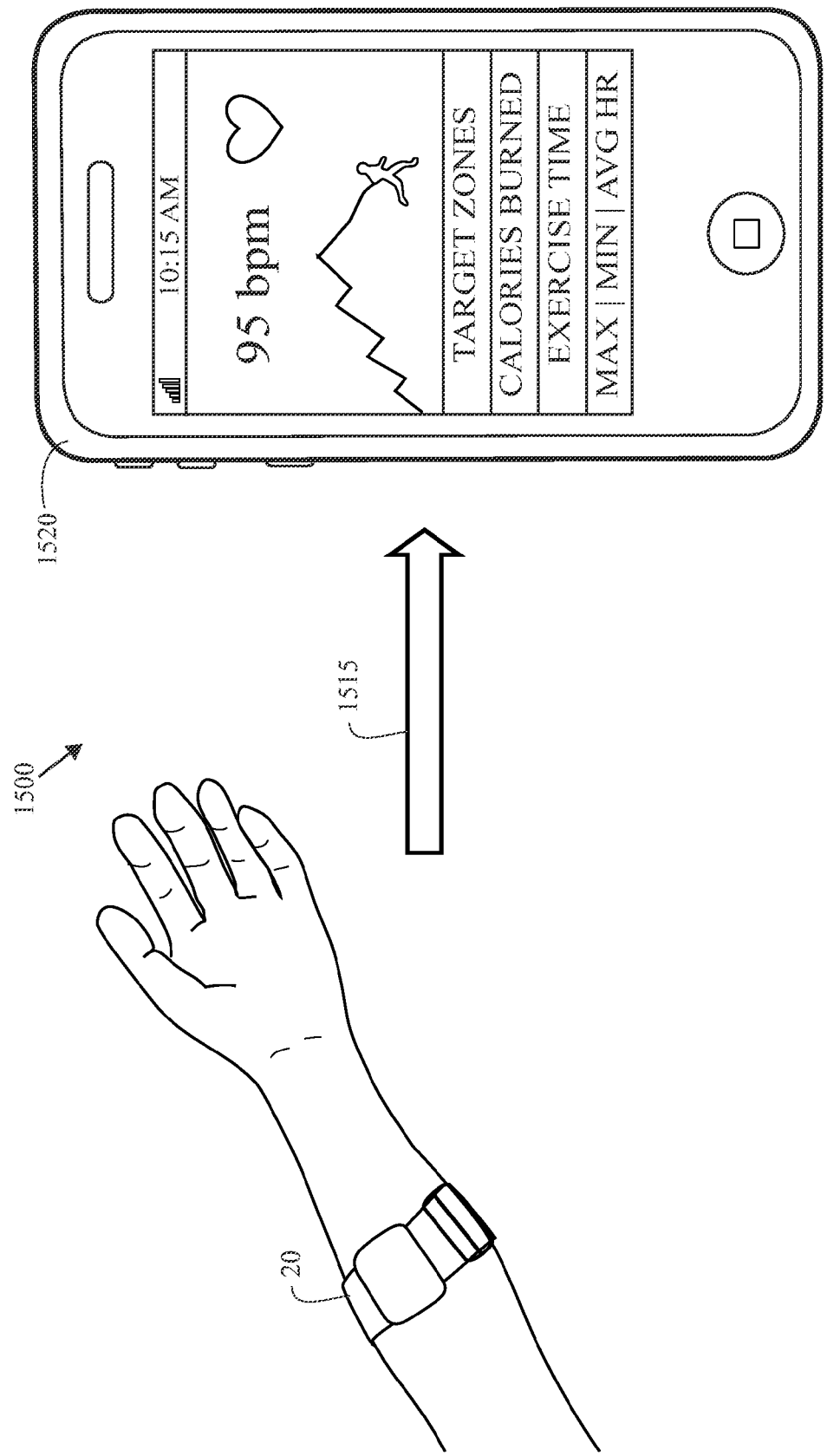
FIG. 26 is an illustration of a system including a monitoring device and a mobile phone which receives a signal from the monitoring device.
Figure 27:
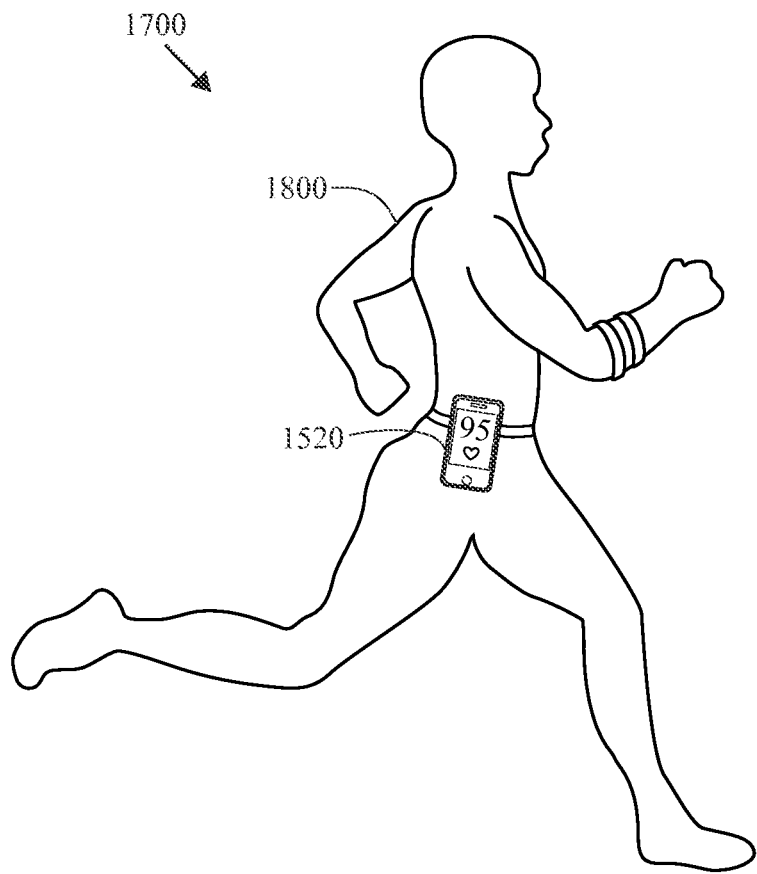
FIG. 27 is an illustration of a runner with a monitoring device and a mobile phone.
Figure 28:
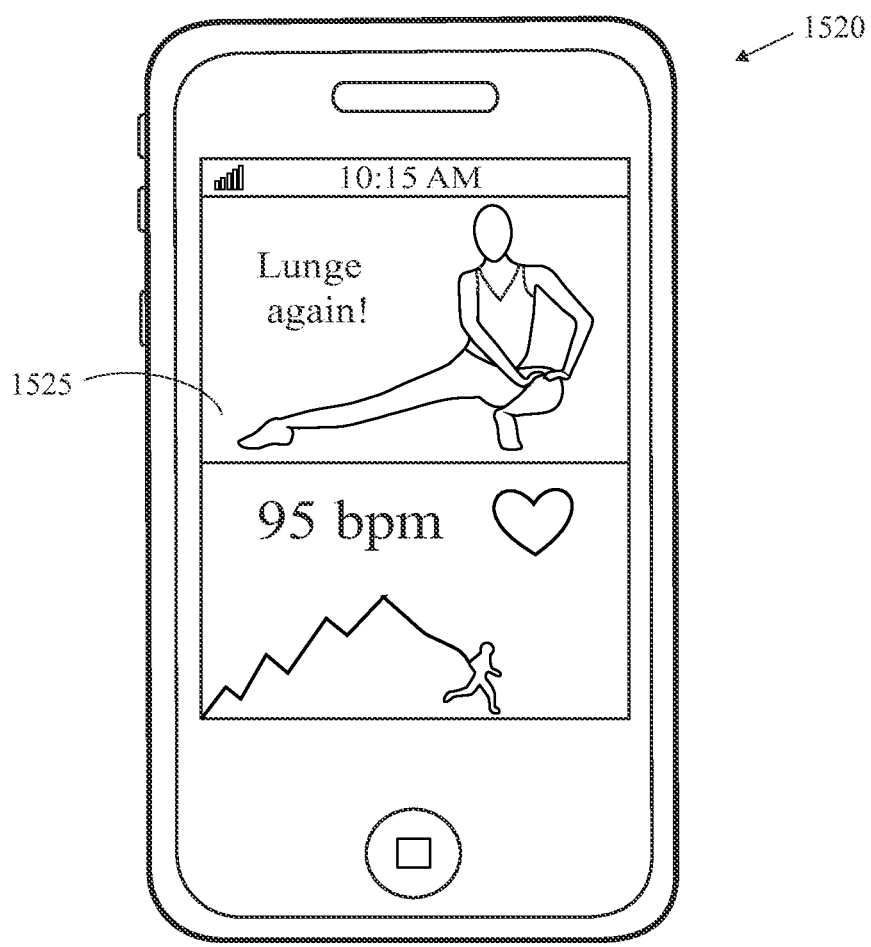
FIG. 28 is an isolated view of a mobile phone with a display of information generated from a signal from a monitoring device.

FIG. 24 illustrates a four cycle Comb filter 3400 with a filter delay of 10, 14, 18, . . . , 4N+2, which is preferably used as at least one of the array of Comb filters 2155 of FIG. 20. The signals begin at input 3410. A collector 3435 sums the signals. A counter 3430 transmits signals to the collector and interpolator 3420. A delay is generated at 3425, sent to the interpolator 3420 and gain 3415 and then a filter delayed signal is sent from output 3440.

Figure 9:
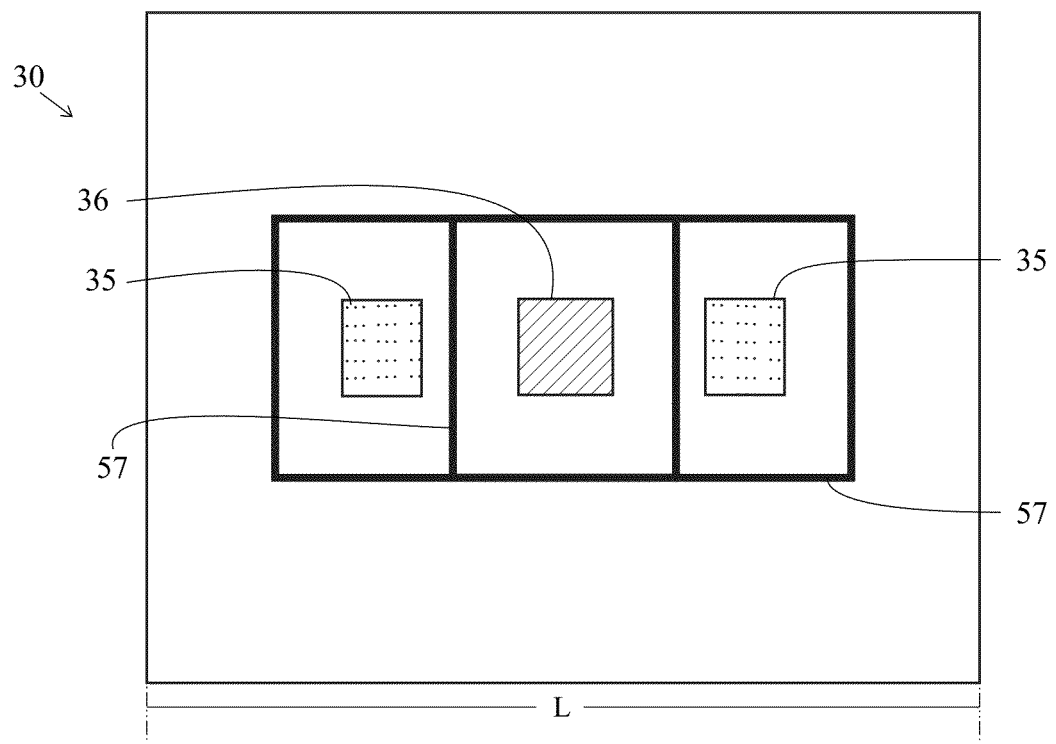
FIG. 9 is an isolated top plan view of an optical sensor for a monitoring device.
Figure 11:
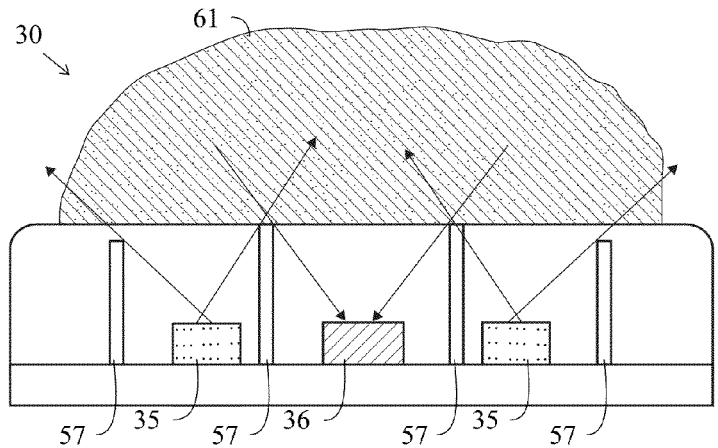
FIG. 11 is an isolated cross section view of an optical sensor for a monitoring device with light reflecting off of an artery of a user.

FIGS. 9-11 illustrate the sensor 30. The sensor 30 has a photodetector 36, at least two LEDs 35 and an opaque light shield 57. The LEDs 35 are preferably green light LEDs. The sensor 30 preferably has a length, L, of 7-10 mm on each side, as shown in FIG. 9. The sensor 30 preferably has a height, H, of 1-1.5 mm, as shown in FIG. 10. The opaque light shield 57 blocks the direct light from the LEDs 35 to the photodetector 36. Only the green light diffused and translucent through the media (skin of the user) 61, as shown in FIG. 11, is allowed to enter the chamber of the photodetector 36. This provides for a more accurate heart rate or vital sign signal.

In a preferred design of the sensor 30, the distance between the centers of active areas of LEDs 35 is preferably 5-6 mm. The active area (photodetector 36) of a sensor 30 is placed in the middle of that distance. In the custom sensor, the distance of a custom sensor is preferably in the range of 3-4 mm (which means the spacing between the centers of photodetector 36 and LEDs 35 is about 1.5-2 mm). The distance is preferably sufficient for the placement of an opaque barrier between them. To control the amplitude of the LED intensity pulse a sufficient current (voltage) range of intensity ramp is used to control the LEDs 35 and to achieve the same levels of intensity in both LEDs 35 within a given range. The electrical characteristics of 520 nm SunLED in terms of voltage range for intensity ramp is sufficient. The top surface of the sensor 30 is preferably flat and in steady contact with the skin. Under a strong motion condition, the skin moves at the border of the contact surface. The sizes of the sensor area and flat skin contact area are selected to reduce the border motion effects. If the distance between the LEDs and sensor is reduced, a lighted area of the skin is smaller, and the contact area is reduced (5×5 mm is acceptable). LGA enables an easy way to seal the contact area from moisture. The preferred embodiment uses 250 microsecond LED pulses and a 12T photodetector 36 with second order active high pass filter (100 Hz cutoff). The DC output of the sensor 30 is monitored to ensure that it is not saturated by the effects of ambient light. The use of short-term pulses reduces ambient light. In the preferred embodiment, voltage is collected at the sensor output every 2 msec. Inside the microprocessor 741, an average 8 consecutive samples improve the SNR (signal to noise ratio) and then work with the averaged numbers. Therefore the sampling rate for raw data is preferably 2 msec, however if 8-samples averaging is utilized in the integrated sensor the data output rate is reduced to sending a new averaged value every 16 msec. An ADC is used with a 12-bit resolution. The response of TSL12T is acceptable. 100 Hz is the low limit for LPF cutoff. The selection of pulse duration is preferably based on the speed of the LED drivers, sensor electronics and output pick detection. The higher the low frequency cutoff that is implemented for the selected pulse duration, the better SNR.

Preferably, two reactance circuits work as load resistances for a photodiode, BPW34. The voltage drop at each reactance circuit is amplified by a differential amplifier, built with two 2N4416 FETs. The symmetrical design makes a diode bias voltage of about 2 V, which is nearly independent of ambient light conditions. The circuit is insensitive to common mode interference. The circuit operates using a single 5 volt power supply.

Figure 12:
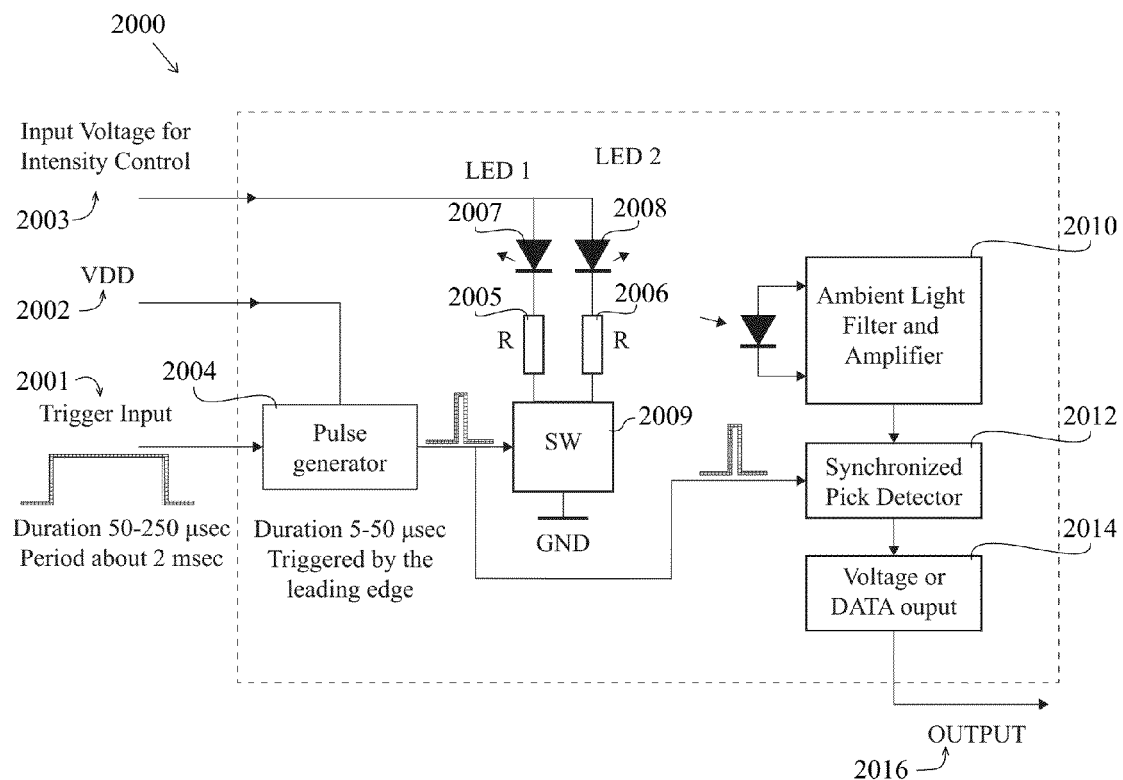
FIG. 12 is a block diagram of electrical components for a monitoring device.

FIG. 12 is a functional block diagram for the signal processing 2000 of the sensor. A trigger input 2001 has a duration of 50-250 microseconds and a period of 2 milliseconds for input to a pulse generator 2004, which also receives input from VDD 2002. Input voltage for intensity control 2003 is sent to resistors 2005 and 2006 and to LEDs 2007 and 2008 and activated by switch 2009. Ambient light filter and amplifier 2010 transits to synchronized pick detector 2012 for a voltage or data output 2014 as an output signal 2016.

As shown in FIGS. 25-28, the system includes a monitoring device 20 and a mobile communication device 1520. The monitoring device 20 transmits data 1515 to the mobile communication device 1520 for display on a screen 1525 of the mobile communication device 1520. The user 1800 preferably wears both the mobile communication device 1520 and the monitoring device 20. Such a mobile communication device preferably includes the IPHONE® smartphone or IPAD™ tablet computer, both from Apple, Inc., BLACKBERRY® smartphones from Research In Motion, the ANDROID® smartphone from Google, Inc., the TRE® smartphone from Palm, Inc., and many more.

One aspect of the present invention is a system for monitoring at least one vital sign of a user. The system comprises a smartphone and a monitoring device. The smartphone comprises a short range wireless transceiver, a processor and a display screen. The monitoring device comprises a housing, an optical sensor for measuring blood flow through an artery of a wrist, arm or ankle of the user, a processor, a short range wireless transceiver, and a power source. The short range wireless transceiver operates on a communication protocol using a 9 kHz communication format, a 125 kHz RFID communication format, a 13.56 MHz communication format, a 433 MHz communication format, a 433 MHz RFID communication format, or a 900 MHz RFID communication format.

Another aspect of the present invention is a method wherein the monitoring device transmits raw data from the optical sensor and the motion sensor to mobile communication device for processing using a signal processing algorithm such as discussed in reference to FIG. 10.

Another aspect of the present invention is a method wherein the monitoring device performs a first filtering of the signals before transmitting the filtered data to the mobile communication device for further processing.

The system and method described herein may be used with an interactive game such as disclosed in Hunt et al., U.S. patent application Ser. No. 13/021,749, filed on Feb. 5, 2011 for a Monitoring Device For An Interactive Game, which is hereby incorporated by reference in its entirety.

A smartphone 1501 receives signals from a heart rate monitor ("HRM") and the display of the smartphone is used to view a user's heart rate ("HR") and to work out to apps and to store data. The HRM simply outputs HR and accelerometer data to the smartphone where a mobile application software ("HRM SW") is processed by the powerful processor of the smartphone. All "heavy" processing and memory is conducted on the smartphone. This reduces the cost, size and power requirements of monitoring device and allows for the more powerful offboard processing, display and storage of HR data by the smatphone. The software application might be a pure fitness app, might be provided by WEIGHT WATCHERS to their clients as an app or could be a game or even medical application for in home use. The game might also require that heart rate reach a certain high or low target before being able to conduct a specified in-game action. For example, a user might have to restore heart rate to their resting baseline before being able to do a high jump. Similarly, they might have to enter a higher target heart zone to "power up" for an attack. HRM application for video game overview: A heart rate monitor would be used as an integral, interactive element of video games to add a degree of realism. A basic example would be in a game that required shooting skills or skills that could be enhanced or degraded by a physical state as indicated by heart rate level. A player's normal heart rate would be measured and entered into a game data base. This average would be used as a baseline to provide more accurate shooting or combat skills if the heart rate was at a lower level during the activity and accuracy would be degraded if the HR was at a certain level above the average. This is reflective of the real world where actual snipers use heart rate as a means to achieve better accuracy. It also is reflective of the real world where a person has to physically move and evade and then fire accurately or engage in other physical combat using manual weapons or personal combat skills. This technique could also be used in sports games such as golf games where shot accuracy could be improved by a lower heart rate or conversely adversely affected by an elevate HR reflecting a nervous or agitated state. The game could encourage and promote the use of interactive biofeedback to control the heart rate and improve performance. In this case the biofeedback training could translate into real world applications for sports or other activities. This application of HR monitoring technology requires a real time heart rate monitor. Such a device may detect the electrical pulses from the heart such as the chest belt monitors, however a preferred application would be a more convenient monitor that would be worn on the arm of the game player, but would be motion resistant as well as continuous.

The communications from the monitoring device to the smartphone is preferably accomplished by using a part 15 low power short range radio, standard Blue tooth or Blue Tooth Low Energy to conserve power or other low power short range communications means. For mobile phones and mobile phone applications the HRM is preferably interactive with Windows operating systems, Apple Operating systems or emergent operating systems such as Android. This facilitates the broadest use in home and in mobile applications.

The monitoring device preferably transmits raw heart rate and accelerometer data to a smartphone. The data is preferably stored or real-time data.

A smartphone application preferably interprets data, displays, and stores it. Such data might include items like heart rate, calories burned, exercise time, max/min/average heart rate, and others. This allows for use of the greater processing power on the smartphone.

Alternatively the monitoring device transmits interpreted data: heart rate, caloric burn exercise session information, exercise time, max/min/average HR info, etc.

The monitoring device alternatively has a display and transmits raw heart rate and accelerometer data to Smart Phone. This may be stored or real-time data.

In this embodiment, the monitoring device displays some data on a display of the monitoring device.

The smartphone application interprets data, displays, and stores it. Such data might include items like heart rate, calories burned, exercise time, max/min/average heart rate, and others. This allows for use of the greater processing power on the smartphone.

Alternatively the monitoring device transmits interpreted data: heart rate, caloric burn exercise session information, exercise time, max/min/average HR info, etc.

A user can run or do other exercise while wearing the monitoring device and the smartphone. The smartphone then becomes a "mobile exercise device.

Users may receive on screen instructions that adjust related to heart rate activity. Instructions may ask user to perform actions which increase/decrease HR.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A system for monitoring a real-time vital sign of a user, the system comprising:

a monitoring device comprising an optical sensor for generating a real-time digitized optical signal corresponding to a flow of blood through an artery of the user, the optical sensor comprising a photodetector, a first LED emitting a green light, a second LED emitting a green light at the same wavelength of the first LED, and an opaque light shield, the opaque light shield preventing the photodetector from receiving direct light from the first LED or the second LED, and only allowing green light diffused and translucent through a skin of the user to be received by the photodetector, wherein the photodetector is positioned an equal distance from the first LED and the second LED, wherein the photodetector is positioned between the first LED and the second LED, wherein the opaque light shield encircles the first LED in a first chamber, the opaque light shield encircles the photodetector in a second chamber, and the opaque light shield encircles the second LED in a third chamber;

an accelerometer for generating a real-time accelerometer data comprising an X-axis signal, a Y-axis signal and a Z-axis signal based on a movement of the user; and a first transceiver for transmitting the real-time digitized optical signal and the real-time accelerometer data from the monitoring device;

a mobile communication device comprising a second transceiver for receiving the real-time digitized optical signal and the real-time accelerometer data from the monitoring device, a processor in electrical communication with the second transceiver, the processor configured to receive the real-time digitized signal and the real-time accelerometer data, the processor configured to generate a real-time heart rate for the user, wherein the processor is configured to filter motion noise from the digital signal utilizing the signal from the accelerometer, process the digital signal to obtain an average pulse value of a first set of time periods, process the digital signal to obtain an average pulse value of a second set of time periods, the second set of time periods less than the first set of time periods, subtract the average pulse value of the second set of time periods from the average pulse value of the first set of time periods to generate a first filtered pulse data value, process the first filtered pulse data value to obtain a first heart rate value, and use the first heart rate value to filter the subsequent average pulse values generated from the digital signal to obtain a real-time heart rate value of the user, and a display for displaying the real-time heart rate value for the user received from the processor.

\* \* \* \* \*